(12) United States Patent
Iinaga

(10) Patent No.: US 10,863,934 B2
(45) Date of Patent: Dec. 15, 2020

(54) BLOOD LIPID CONCENTRATION MEASUREMENT DEVICE AND METHOD FOR OPERATING SAME

(71) Applicant: MEDICAL PHOTONICS CO., LTD., Hokkaido (JP)

(72) Inventor: Kazuya Iinaga, Sapporo (JP)

(73) Assignee: MEDICAL PHOTONICS CO., LTD., Hokkaido (JP)

(*) Notice: Subject to any disclaimer, the term of this patent is extended or adjusted under 35 U.S.C. 154(b) by 268 days.

(21) Appl. No.: 16/301,108

(22) PCT Filed: Feb. 14, 2017

(86) PCT No.: PCT/JP2017/005355
§ 371 (c)(1),
(2) Date: Nov. 13, 2018

(87) PCT Pub. No.: WO2017/199492
PCT Pub. Date: Nov. 23, 2017

(65) Prior Publication Data
US 2019/0192056 A1    Jun. 27, 2019

(30) Foreign Application Priority Data
May 18, 2016   (JP) ................................. 2016-099499

(51) Int. Cl.
*A61B 5/1455*   (2006.01)
*G01N 21/17*   (2006.01)
(Continued)

(52) U.S. Cl.
CPC ........ *A61B 5/1455* (2013.01); *A61B 5/14546* (2013.01); *A61B 5/7271* (2013.01); *G01N 21/17* (2013.01)

(58) Field of Classification Search
CPC ..... A61B 5/1455; A61B 5/14546; A61B 5/72; A61B 5/7271; A61B 5/0059
See application file for complete search history.

(56) References Cited

U.S. PATENT DOCUMENTS

| | | | |
|---|---|---|---|
| 6,615,061 B1 * | 9/2003 | Khalil ................ | A61B 5/14532 600/310 |
| 2014/0012103 A1 | 1/2014 | Nishida et al. | |
| 2015/0313516 A1 | 11/2015 | Shimizu et al. | |

FOREIGN PATENT DOCUMENTS

| | | |
|---|---|---|
| EP | 3 417 779 | 12/2018 |
| JP | 2007-117221 | 5/2007 |

(Continued)

OTHER PUBLICATIONS

Extended European Search Report dated Apr. 15, 2020 in corresponding European Patent Application No. 17798930.8.
(Continued)

*Primary Examiner* — Eric F Winakur
(74) *Attorney, Agent, or Firm* — Wenderoth, Lind & Ponack, L.L.P.

(57) ABSTRACT

A device and method for measuring levels of individual lipids in a lipoprotein, the device being equipped with: an irradiation unit that can emit irradiation light having a first wavelength and irradiation light having a second wavelength at predetermined light intensities toward the inside of a living body from outside of the living body; a light intensity detection unit arranged at a predetermined distance apart from a position at which light is emitted from the irradiation unit or is arranged adjacent to the position, and can detect the intensities of first light and second light both emitted from the living body; a scattering coefficient calculation unit that can calculate a first scattering coefficient and a second scattering coefficient in the living body respectively on the basis of the intensities of a first light and a second light (Continued)

detected by the light intensity detection unit; and a lipid level calculation unit.

20 Claims, 8 Drawing Sheets

(51) Int. Cl.
   *A61B 5/00* (2006.01)
   *A61B 5/145* (2006.01)

(56) References Cited

FOREIGN PATENT DOCUMENTS

| JP | 2010-048703 | 3/2010 |
| WO | 2014/087825 | 6/2014 |
| WO | 2016/041073 | 3/2016 |

OTHER PUBLICATIONS

Search Report dated Apr. 23, 2020 in corresponding Taiwanese Patent Application No. 105143548, with English Translation.
Kazuya Iinaga et al., "Attempt for Noninvasive Evaluation of in vivo Triglyceride in Blood", 2014 36th Annual International Conference of the IEEE engineering in Medicine and Biology Society, Jul. 1, 2013, vol. 2013, pp. 1214-1217, XP055605275.
Suchin Trirongjitmoah et al., "Practical technique to quantify small, dense low-density lipoprotein cholesterol using dynamic light scattering", Optical Review, Feb. 5, 2016, vol. 23, No. 2, pp. 265-272, XP055605295.
Kazuya Iinaga et al., "Estimation of scattering coefficient in CW reflectance measurement for noninvasive triglyceride evaluation", 2013 Conference on Lasers and Electro-Optics Pacific Rim (CLEO-PR), Jun. 30, 2013, pp. 1-2, XP032481602.
International Search Report dated Apr. 11, 2017 in International (PCT) Application No. PCT/JP2017/005355.

\* cited by examiner

BLOOD LIPID CONCENTRATION MEASUREMENT DEVICE AND METHOD FOR OPERATING SAME

TECHNICAL FIELD

The present invention relates to a device configured to measure a lipid concentration in the blood and a method for operating the same.

BACKGROUND ART

Controlling the public medical care expenditure is a great concern. A treatment cost of a disease caused by a life style disease accounts for one-third of the medical care expenditure. It is required to extend a healthy life expectancy and improve QOL in order to control the public medical care expenditure. For this purpose, a specific medical examination has been implemented and people become more aware of a presymptomatic disease.

In particular, it is known that a metabolic syndrome, which is a screening target of the specific medical examination, develops diabetes, dyslipidemia, and hypertension caused by a metabolic disorder due to accumulation of visceral fat obesity. It is expected that early detection of the metabolic syndrome leads to prevention of disease progression, improvement of QOL, and control of the public medical care expenditure.

As described above, the metabolic disorder is important for early detection of the life style disease, however, measuring abdominal girth is the only available method for predicting a risk of insulin resistance in the specific medical examination. This is because it has been difficult to instantly measure the metabolism of a living body with a conventional examination method involving blood collection. Moreover, it has been difficult to measure a blood component without collecting blood.

A lipid in the blood, due to its high hydrophobicity, forms a micelle covered with an amphiphilic phospholipid and exits in a particle form. The particle has a lipoprotein bound to its surface and is thus called a lipoprotein.

The lipoproteins are roughly classified into four types on the basis of their specific gravities. The lipoproteins are classified as chylomicron (CM), VLDL, LDL, and HDL in increasing order of their specific gravities. Further, the lipoproteins are classified as CM, VLDL, LDL, and HDL in decreasing order of their particle diameters.

The lipoprotein is an assembly of a cholesterol and a triglyceride (TG). A blood test measures the triglyceride and the cholesterol which are a minimum unit of a constituent component of the lipoprotein.

For example, an LDL cholesterol called a bad cholesterol is a cholesterol concentration included in an LDL particle. Measuring TG in the LDL particle gives LDL-TG. In particular, the LDL cholesterol and an HDL cholesterol are known to be an indicator related to arteriosclerosis.

In recent years, important symptoms in measuring the metabolism include postprandial hyperlipidemia. Postprandial hyperlipidemia draws attention as a risk factor for arteriosclerosis. It has been reported that a coronary heart disease event onset risk becomes higher as a non-fasting triglyceride concentration increases.

However, the diagnosis of postprandial hyperlipidemia requires observation of a change in a blood lipid concentration for 6 to 8 hours after eating. That is, in order to measure a state of hyperlipemia after eating, an examinee needs to be held for 6 to 8 hours to collect the blood multiple times. Thus, the diagnosis of postprandial hyperlipidemia can be implemented only in clinical research and cannot be implemented in clinical practice in reality.

Patent Literature 1 discloses a method for solving such a problem. The method in Patent literature 1 does not require blood collection and allows a blood lipid to be measured not only in a medical facility but also at home. Since data can be instantly acquired, the blood lipid can be measured in a continuous-time manner.

CITATION LIST

Patent Literature

Patent Literature 1: WO2014/087825

SUMMARY OF INVENTION

Technical Problem

However, the method in Patent Literature 1, which measures the lipid concentration of the entire lipoproteins, cannot measure individual concentrations of CM, VLDL, LDL, and HDL. This means that the method in Patent Literature 1 hardly obtains accurate information for determining a physical condition by measuring the four types of lipoproteins as a total though they have distinctive roles in the living body. Specifically, a lack of clarity in specifying a measurement object may cause problems, such as misjudgment in evaluating a disease and a physical condition, and ambiguous data interpretation.

The present invention has been made to solve such conventional problems and provides a device and a method for separately measuring individual lipoproteins or measuring lipid concentrations in individual lipoproteins by non-invasive lipid measurement.

Solution to Problem

A blood lipid concentration measurement device of the present invention includes: an irradiation portion configured to irradiate irradiation light having a first wavelength and irradiation light having a second wavelength shorter than the first wavelength at predetermined light intensities toward an inside of a living body from an outside of the living body; a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion; a scattering coefficient calculation portion configured to calculate a first scattering coefficient and a second scattering coefficient in the living body respectively on the basis of the first light intensity and the second light intensity detected by the light intensity detection portion; and a lipid concentration calculation portion configured to calculate a variation of a concentration of a second lipid group in the blood on the basis of a variation of the second scattering coefficient and calculate a variation of a concentration of a first lipid group including a lipid whose particle diameter is equal to or less than that of a lipid included in the second lipid group on the basis of a variation of the first scattering coefficient.

Further, a blood lipid concentration measurement device of the present invention includes: an irradiation portion configured to radiate irradiation light having a wavelength of 900 nm or less at a predetermined light intensity toward an inside of a living body from an outside of the living body; a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion; a scattering coefficient calculation portion configured to calculate a scattering coefficient in the living body on the basis of the light intensity detected by the light intensity detection portion; and a lipid concentration calculation portion configured to calculate a variation of only a concentration of at least one of CM and a CM remnant in the blood on the basis of a variation of the scattering coefficient.

Further, a method for operating a blood lipid concentration measurement device of the present invention includes: an irradiation step of radiating irradiation light having a first wavelength and irradiation light having a second wavelength shorter than the first wavelength at predetermined light intensities toward an inside of a living body from an outside of the living body; a light intensity detection step of detecting an intensity of first light and an intensity of second light both emitted from the living body to measure a radiation-detection distance dependent attenuation of light intensities of the radiated irradiation light having the first wavelength and the radiated irradiation light having the second wavelength at a position with a predetermined interval from or continuously to a light irradiation position in the irradiation step; a scattering coefficient calculation step of calculating a first scattering coefficient and a second scattering coefficient in the living body respectively on the basis of the first light intensity and the second light intensity detected in the light intensity detection step; and a lipid concentration calculation step of calculating a variation of a concentration of a second lipid group in the blood on the basis of a variation of the second scattering coefficient and calculating a variation of a concentration of a first lipid group including a lipid whose particle diameter is equal to or less than that of a lipid included in the second lipid group on the basis of a variation of the first scattering coefficient.

Further, a method for operating a blood lipid concentration measurement device of the present invention includes: an irradiation step of radiating irradiation light having a wavelength of 900 nm or less at a predetermined light intensity toward an inside of a living body from an outside of the living body; a light intensity detection step of detecting an intensity of light emitted from the living body to measure a radiation-detection distance dependent attenuation of a light intensity of the radiated irradiation light at a position with a predetermined interval from or continuously to a light irradiation position in the irradiation step; a scattering coefficient calculation step of calculating a scattering coefficient in the living body on the basis of the light intensity detected in the light intensity detection step; and a lipid concentration calculation step of calculating a variation of a concentration of at least one of CM and a CM remnant in the blood on the basis of a variation of the scattering coefficient.

Further, a blood lipid concentration measurement device of the present invention is communicatively connected to a user device that includes: an irradiation portion configured to radiate irradiation light having a first wavelength and irradiation light having a second wavelength shorter than the first wavelength at predetermined light intensities toward an inside of a living body from an outside of the living body; a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion; and a communication portion configured to send the first light intensity and the second light intensity detected by the light intensity detection portion, the blood lipid concentration measurement device including: a scattering coefficient calculation portion that calculates a first scattering coefficient and a second scattering coefficient in the living body respectively on the basis of the first light intensity and the second light intensity sent from the user device; and a lipid concentration calculation portion configured to calculate a variation of a concentration of a second lipid group in the blood on the basis of a variation of the second scattering coefficient and calculate a variation of a concentration of a first lipid group including a lipid whose particle diameter is equal to or less than that of a lipid included in the second lipid group on the basis of a variation of the first scattering coefficient.

Further, a blood lipid concentration measurement device of the present invention is communicatively connected to a user device that includes: an irradiation portion configured to radiate irradiation light having a wavelength of 900 nm or less at a predetermined light intensity toward an inside of a living body from an outside of the living body; a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion; and a communication portion configured to send the light intensity detected by the light intensity detection portion, the blood lipid concentration measurement device including: a scattering coefficient calculation portion configured to calculate a scattering coefficient in the living body on the basis of the light intensity sent from the user device; and a lipid concentration calculation portion configured to calculate a variation of only a concentration of at least one of CM and a CM remnant in the blood on the basis of a variation of the scattering coefficient.

Advantageous Effects of Invention

The blood lipid concentration measurement device and the operation method thereof of the present invention make it possible to measure concentrations of individual lipids included in the lipoproteins by the non-invasive lipid measurement using a plurality of wavelengths.

DESCRIPTION OF EMBODIMENTS

First Embodiment

Figure 1:
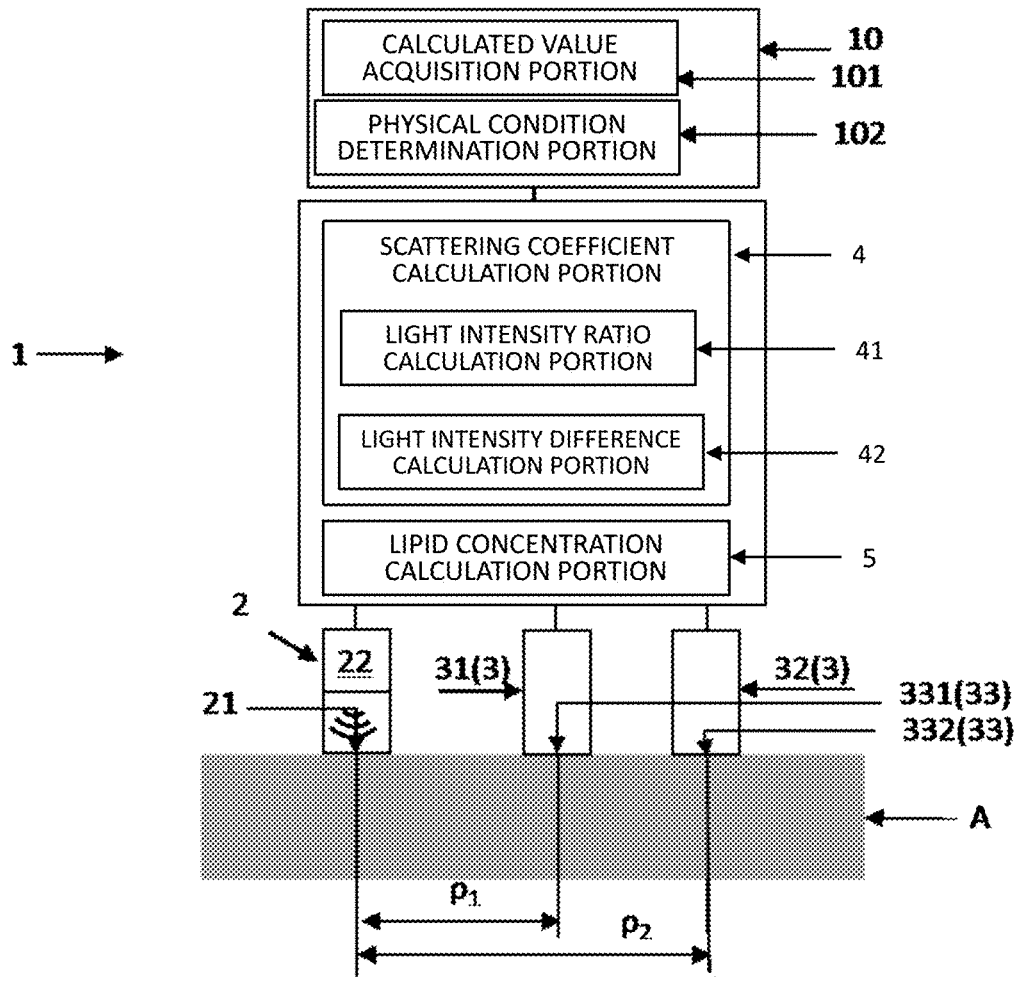
FIG. 1 is a diagram illustrating a configuration of a blood lipid concentration measurement device of the present embodiment.

Hereinafter, a blood lipid concentration measurement device and an operation method thereof as a first embodiment of the present invention will be described in detail by referring to the drawings.

FIG. 1 is a diagram illustrating a configuration of a blood lipid concentration measurement device of the present embodiment. The blood lipid concentration measurement device of the present embodiment includes a CPU (arithmetic unit) and a memory device (storage unit such as a RAM and a ROM) and functions as a device shown in a block diagram in FIG. 1 by executing a program stored in the memory device.

FIG. 1 is a block diagram illustrating the configuration of the blood lipid concentration measurement device of the present embodiment. As shown in FIG. 1, a blood lipid concentration measurement device 1 includes: an irradiation portion 2 configured to radiate irradiation light toward a living body (A in the drawing) from an outside of the living body; a light intensity detection portion 3 configured to detect a light intensity at a predetermined detection position 31 outside the living body; a scattering coefficient calculation portion 4 configured to calculate a light scattering coefficient μs' in the living body on the basis of the light intensity detected by the light intensity detection portion 3; a lipid concentration calculation portion 5 configured to calculate a lipid concentration in the living body on the basis of the light scattering coefficient μs' calculated by the scattering coefficient calculation portion 4, and a physical condition management measurement device 10 configured to determine a physical condition on the basis of the lipid concentration.

As shown in FIG. 1, the irradiation portion 2 includes a light source 22 configured to radiate irradiation light to a predetermined irradiation position 21 toward the inside of the living body from the outside of the living body. The light source 22 of the present embodiment can adjust a wavelength of the irradiation light. The light source 22 can adjust the wavelength to be outside a wavelength range in which light is absorbed by an inorganic matter in the blood plasma. The light source 22 can adjust the wavelength to be outside a wavelength range in which light is absorbed by a cellular component in the blood. The cellular component in the blood described herein refers to a red corpuscle, a white corpuscle, and a platelet in the blood. The inorganic matter in the blood plasma refers to water and an electrolyte in the blood.

The light source 22 of the present embodiment radiates the irradiation light having the first wavelength and the irradiation light having the second wavelength shorter than the first wavelength. The blood lipid concentration measurement device 1 of the present embodiment radiates the irradiation light having different wavelengths into the blood to measure concentrations of individual lipids having different particle diameters.

Herein, the first wavelength is preferably 750 nm or more and the second wavelength is preferably shorter than the first wavelength and 900 nm or less. Note that a reason for measuring light intensities using two wavelengths having a boundary value between 750 nm and 900 nm will be described in Examples.

Further, the irradiation portion 2 of the present embodiment can freely adjust a time length of radiation of light, such as radiation of continuous light and radiation of pulsed light, in accordance with a calculation method of the scattering coefficient μs' performed by the scattering coefficient calculation portion 4 described below. The irradiation portion 2 can freely modulate an intensity or phase of light to be radiated.

The light intensity detection portion 3 receives the irradiation light having the first wavelength emitted from the living body to the outside of the living body to detect the first light intensity. The light intensity detection portion 3 receives the irradiation light having the second wavelength emitted from the living body to the outside of the living body to detect the second light intensity. In a case where a plurality of light intensity detection portions 3 are used, the light intensity detection portions 3 are disposed at different distances from the irradiation position 21 as a substantial center. As shown in FIG. 1, in the present embodiment, a first light intensity detection portion 31 and a second light intensity detection portion 32 are arranged in this order in a straight line on the same plane at predetermined intervals from the irradiation position 21. The light intensity detection portion 3 may be a light receiving element such as a CCD or a CMOS.

As shown in FIG. 1, in the present embodiment, a distance from the irradiation position 21 to a first detection position 331 of the first light intensity detection portion 31 is defined as a first radiation-detection distance ρ1 and a distance from the irradiation position 21 to a second detection position 332 of the second light intensity detection portion 32 is defined as a second radiation-detection distance ρ2.

Figure 2:
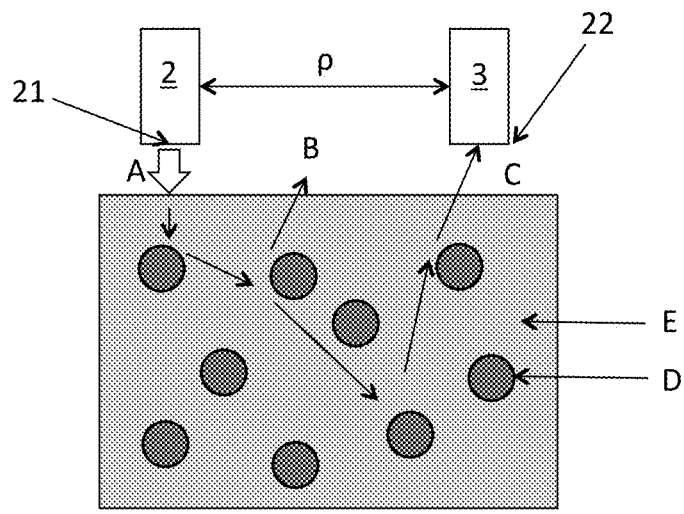
FIG. 2 is a diagram illustrating light scattering caused by blood lipids.

As shown in FIG. 2, a predetermined distance p is provided between the irradiation position 21 where the light is radiated to the living body and the detection position 31 where the intensity of the light emitted from the blood (E in the drawing) in the living body is detected. Providing the predetermined distance p prevents an influence of light (B in the drawing) directly emitted from the living body due to reflection of the radiated light (A in the drawing) by a scattering body on or near a surface of the living body. The radiated light reaches a depth where lipids such as lipoproteins are present and is then reflected by the lipids (D in the drawing) in the blood.

The light reflected by the lipids is scattered and emitted from the living body as back scattered light (C in the drawing). The light intensity of the back scattered light is detected. Further, extending the distance ρ between the irradiation position 21 and the detection position 31 extends an optical path length. Thus, the light to be detected collides with the lipids more frequently and is greatly influenced by the scattering. Extending the distance ρ facilitates detection of an influence of the scattering that have been hardly detected due to faintness heretofore.

The lipoprotein as a measurement object has a spherical structure covered with an apoprotein and the like. The lipoprotein behaves like a solid matter in the blood. The lipoprotein has light reflectivity. In particular, chylomicron (CM), VLDL, and the like, having a large particle diameter and specific gravity, contain a large amount of triglycerides (TG) and have characteristics of further facilitating the scattering of light. Thus, the light intensity detected by the light intensity detection portion 3 includes the influence of the light scattering caused by the lipoprotein.

Note that, in a case where a plurality of the detection positions 31 are arranged, a layout thereof is not limited to a linear form as long as they are arranged at different distances from the irradiation position 21 serving as the substantial center. The layout may be appropriately selected from a circular form, a wave form, a zigzag form, and the like. Further, the first radiation-detection distance ρ1 between the irradiation position 21 and the detection position 31, the second radiation-detection distance ρ2, and an interval between the detection positions 331 and 332 are not limited to certain intervals and they may be arranged continuously to each other.

The scattering coefficient calculation portion 4 calculates a first scattering coefficient μs1' in the living body (including the blood, the skin, the muscle, etc., hereinafter the same) on the basis of the first light intensity detected by the light intensity detection portion 3. The scattering coefficient calculation portion 4 calculates a second scattering coefficient μs2' in the living body on the basis of the second light intensity detected by the light intensity detection portion 3.

As described above, the first and second light intensities detected by the light intensity detection portion 3 include the influence of the light scattering caused by the lipoprotein. This feature is utilized to calculate the first scattering coefficient μs1' and the second scattering coefficient μs2'. Hereinbelow, the first scattering coefficient μs1' and the second scattering coefficient μs2' are simply referred to as a scattering coefficient μs' if they do not need to be distinguished.

Note that the scattering coefficient μs' in the present embodiment is not limited to a value obtained by quantifying an efficiency of a general scattering process and includes a value obtained by quantifying an influence of the scattering under a predetermined condition in consideration of a scattering phenomenon.

As shown in FIG. 1, the scattering coefficient calculation portion 4 in the present embodiment includes two calculation portions, namely, a light intensity ratio calculation portion 42 and a light intensity difference calculation portion 43.

The light intensity ratio calculation portion 42 calculates the scattering coefficient μs' from a ratio between the light intensities detected by the plurality of light intensity detection portions 3. The light intensity ratio calculation portion 42 calculates the scattering coefficient μs' on the basis of the scattering phenomenon in which the radiated light is more attenuated by the scattering as the distance to a detection position 33 is increased.

In the present embodiment, continuous light having a predetermined light intensity is radiated by the irradiation portion 2 and the scattering coefficient μs' is calculated from a ratio between a light intensity R(ρ1) detected by the first light intensity detection portion 31 and a light intensity R(ρ2) detected by the second light intensity detection portion 32 (Equation 1).

$$\mu s'=R(\rho 1)/R(\rho 2) \tag{Equation 1}$$

The light intensity difference calculation portion 43 calculates the scattering coefficient μs' from a difference between the light intensities detected by the plurality of light intensity detection portions 3. As with the light intensity ratio calculation portion 42, the scattering coefficient μs' is calculated on the basis of the scattering phenomenon in which the radiated light is more attenuated by the scattering as the distance to the detection position 33 is increased.

The light intensity difference calculation portion 43 in the present embodiment calculates the scattering coefficient μs' from a difference between the light intensity R (ρ1) at the first detection position 331 and the light intensity R (ρ2) at the second detection position 332 (Equation 2).

$$\mu s'=R(\rho 1)-R(\rho 2) \tag{Equation 2}$$

Note that the calculation method of the scattering coefficient μs' by the scattering coefficient calculation portion 4 is not limited to the calculations described above.

The lipid concentration calculation portion 5 calculates a variation C2 of a blood concentration of the second lipid group including at least one type of lipids (for example, CM and a CM remnant) from a variation of the second scattering coefficient μs2' calculated by the scattering coefficient calculation portion 4. Note that the remnant refers to a lipid whose diameter is reduced by metabolism. Further, the lipid concentration calculation portion 5 calculates a variation C1 of a blood concentration of the first lipid group including at least one type of lipids whose particle diameter is equal to or less than that of the lipid included in the second lipid group (for example, CM, a CM remnant, VLDL, and a VLDL remnant) from a variation of the first scattering coefficient μs1' calculated by the scattering coefficient calculation portion 4. The lipid concentration calculation portion 5 calculates a variation (C1-C2) of a concentration of the lipid that is not duplicated between the first lipid group and the second lipid group (for example, VLDL and a VLDL remnant) from a difference between the variation C1 of the concentration of the first lipid group and the variation C2 of the concentration of the second lipid group.

Figure 3:
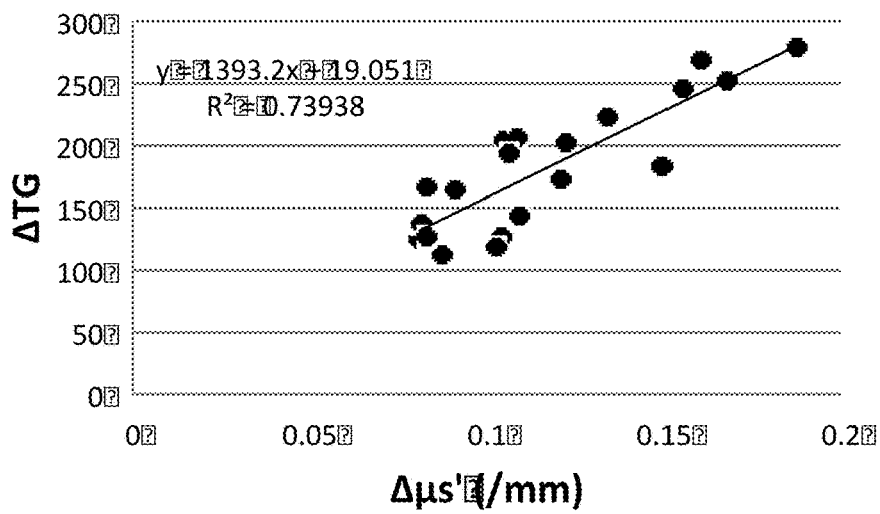
FIG. 3 is a diagram illustrating a correlation between a variation of a scattering coefficient μs' of lipids and a lipid concentration.

As shown in FIG. 3, it can be seen that there is a correlation between a variation of the scattering coefficient μs' (Δμs' in a horizontal axis in FIG. 3) and a variation of the lipid concentration (ΔTG in a vertical axis in FIG. 3). Thus, the variation of the lipid concentration can be calculated on the basis of the variation of the scattering coefficient μs'. Note that, although linear approximation is used in FIG. 3, other approximation methods such as curve approximation may be appropriately used.

In the present embodiment, the variation of the lipid concentration is calculated by obtaining, in advance, statistical data on a relation between the variation of the scattering coefficient μs' and the variation of the blood concentration of the lipoproteins and comparing the variation of the scattering coefficient μs' measured using the present device and the above statistical data.

For example, in a case where a blood lipid concentration of a certain living body (Mr. A) is a measurement object, the variation of the lipid concentration can be calculated by comparing a measurement result of the variation of the blood lipid concentration of Mr. A, which is measured by another blood lipid concentration measurement method, such as blood collection, with the calculated variation of the scattering coefficient μs' and then creating personal statistical data for Mr. A.

Alternatively, the personal statistical data for Mr. A may be created by comparing the measurement result of the variation of the blood lipid concentration of Mr. A, which is measured by another blood lipid concentration measurement method or the like, with a measurement result of the variation of the lipid concentration obtained from the detected light intensity, calculating an error between the variation of the lipid concentration obtained by this comparison and a variation of the lipid concentration in a common living body obtained from statistical data, and then performing calibration for correcting the error.

Further, in clinical practice, the term "concentration" and the term "turbidity" are sometimes used synonymously, and thus the term "concentration" used in the present embodiment includes the meaning of turbidity. Thus, the calculation result of the lipid concentration calculation portion 5 may represent not only the concentration, but also the particle number per unit quantity, formazin turbidity, or a variation of the average particle diameter of the lipids.

Note that a format of the statistical data is not particularly limited, and may be classified by, for example, gender, height, weight, and BMI. The statistical data may be calculated using a table, a graph, a function expression, and the like.

Further, a reason why the variation C2 of the blood concentration of the second lipid group including at least one type of lipids (for example, CM and a CM remnant) can be calculated from the variation of the second scattering coefficient μs2' and the variation C1 of the blood concentration of the first lipid group including at least one type of lipids (for example, CM, a CM remnant, VLDL, and a VLDL remnant) whose particle diameter is equal to or less than that of the lipid included in the second lipid group can be calculated from the variation of the first scattering coefficient μs1' will be described in Examples below.

The lipid concentration calculation portion 5 may calculate the variation (C1-C2) of the concentration of the lipid that is not duplicated between the first lipid group and the second lipid group (for example, VLDL and a VLDL remnant) from the variation C1 of the concentration of the first lipid group and the variation C2 of the concentration of the second lipid group. This allows more accurate evaluation of lipid behavior.

CM and CM-R (a CM remnant, hereinafter the same) are recently recognized as a risk of arteriosclerosis, however, VLDL-R (a VLDL remnant, hereinafter the same) was already recognized as a risk of arteriosclerosis 2 to 3 years ago. Further, it is speculated that an onset mechanism of arteriosclerosis is different between a CM-based lipid and a VLDL-based lipid, thus different medicines need to be administered. For example, a fat absorption inhibitor, which can suppress an increase of CM and CM-R, fails to exhibit a medication effect on VLDL or the like whose level is increased by alcohol.

Further, CM and CM-R causes a problem by not being absorbed by adipocyte and hepatocyte. CM and CM-R not absorbed by either cell have nowhere to go and end up being absorbed in the blood vessel. On the other hand, VLDL, which is originally secreted from the liver, indicates a discharging ability of triglyceride in the liver. If an amount of VLDL is small relative to an amount of CM, it may suggest that fats tend to accumulate in the liver.

Further, although VLDL is a preliminary stage of LDL, VLDL rich in TG becomes sd-LDL known as a risk factor of arteriosclerosis instead of LDL. VLDL with a relatively large size (with a significant change in particle diameter) may suggest an increase in the risk of arteriosclerosis and can be also used as an indicator for selecting a medicine that prevents enlargement of VLDL.

The physical condition management measurement device 10 determines a lipid metabolic state and a physical condition by acquiring the variation C1 of the concentration of the first lipid group, the variation C2 of the concentration of the second lipid group, and the difference therebetween (C1-C2) calculated by the lipid concentration calculation portion 5. As shown in FIG. 1, the physical condition management measurement device 10 of the present embodiment is connected to the lipid concentration calculation portion 5 via a communication line or the like. The physical condition management measurement device 10 includes a calculated-value acquisition portion 101 configured to acquire the lipid concentration calculated by the lipid concentration calculation portion 5 at specified time intervals and a physical condition determination portion 102 configured to determine the lipid metabolic state and the physical condition in accordance with a temporal change in the lipid concentration acquired by the calculated-value acquisition portion 101.

Note that time intervals of acquiring the variation of the lipid concentration by the calculated-value acquisition portion 101 are not particularly limited, and time intervals may be adjusted to intervals of several milliseconds to several tens of minutes, or more, in accordance with a test object.

Further, acquisition of the variation of the lipid concentration is not limited to a method via the communication line, and it may be acquired by manually inputting the variation of the lipid concentration calculated by the lipid concentration portions calculation 5. Further, in the present embodiment, the lipid concentration calculation portion 5 and the physical condition management measurement device 10 are separately configured, however, they may be integrally configured.

The physical condition determination portion 102 determines the physical condition of an examinee, for example, from the temporal changes in the variations of the lipid concentrations of the first lipid group and the second lipid group acquired by the calculated-value acquisition portion 101.

For example, in a case where the first lipid group includes CM and VLDL (and their remnants) and the second lipid group includes CM (and its remnant), a total absorption amount of alcohol or fats can be determined from the temporal change in the variation of the concentration of VLDL (and its remnant) which is obtained from the difference between the variations of the concentrations of the first lipid group and the second lipid group. This facilitates the application of the device to a health management and a dietary management.

For example, the concentration changes in CM and VLDL (and their remnants) are currently used as an evaluation indicator for a food for specified health uses. A variation of the triglyceride is measured after eating to confirm a triglyceride increase inhibitory effect of indigestible dextrin, which is an active ingredient of a soft drink, after eating. (See, for example, Effects of Carbonated Beverage Containing Resistant Maltodextrin on Postprandial Serum Triglyceride, Yuki Shinoda., et, al. p 1031-1038 Jpn Pharmacol Ther Vol. 43 no. 7 2015.)

Further, an area of a temporal change in the triglycerides (an area under the curve (AUC) of blood concentration) is also used as an evaluation indicator. Specifically, it is used as an evidence evaluation indicator for a food for specified health uses and a functional food. (See, for example, A Study on the Effects of Powdered Black Tea Containing Polydextrose on Postprandial searum Trigriceride, Akira Takano., et, al. p 1149-p 1156 Jpn Pharmacol Ther Vol. 43 no. 8 2015.) These methods examine the variation of the triglycerides after eating (after a fat loading test), and the measuring objects are considered to be the same as that of the non-invasive lipid measurement device.

It has been pointed out that CM-R is associated with and a causative of arteriosclerosis. (See, for example, "Dyslipidemia treatment Q&A" published by Japan atherosclerosis society (general incorporated association), the Internet <URL: http://www.j-athero.org/ganda/>), and "Postprandial hyperlipidemia and remnants (No. 2), a significance of measuring remnants in the metabolic syndrome", Approach to diseases (VOL. 34), Clinical and Laboratory, VOL. 38, published by Fukuoka city medical association clinical laboratory center, the Internet <URL; http://www.city.fukuoka.med.or.jp/kensa/ensinbunri/enshin_38_x.pdf>.)

Changes in concentrations of CM and CM-R are a risk factor for arteriosclerosis, thus a risk of arteriosclerosis can be determined from a temporal change in a concentration of at least one of CM and a CM remnant. CM and CM-R are examined by their residence times. If CM-R is not absorbed in the liver due to abnormality in CM-R (or in the liver), CM-R is absorbed inside the blood vessel and causes arteriosclerosis. Eventually, these factors are comprehensively judged to determine a comprehensive health condition.

The physical condition determination portion 102 determines a course of action to improve a balance of the lipids (CM, VLDL) from the difference between the variation of the concentration of the first lipid group and the variation of the concentration of the second lipid group. The course of action includes a nutritional guidance, an exercise guidance, and a selection of supplements in a non-medical field, and includes a selection of medicines, a treatment course, and a diagnosis of diseases in a medical filed.

The blood lipid concentration measurement device 1 of the present embodiment may include a current application portion that applies a pulse current to the inside of the living body. A lipid particle is charged and has a different zeta potential depending on a type of the lipoprotein. By utilizing such a feature, CM or VLDL is caused to vibrate by applying the pulse current to the inside of the body from the outside of the body using the current application portion. This causes a change in the scattering coefficient and allows more accurate measurement of the distribution of the lipoproteins.

Further, the blood lipid concentration measurement device 1 of the present embodiment can be applied for measuring LDL and HDL by using light having a wavelength longer than the first wavelength described above. Thus, the blood lipid concentration measurement device 1 of the present embodiment is not limited to the measurement of the combination of CM and VLDL, and it can be applied for the measurement of other lipids having different particle diameters.

Figure 4:
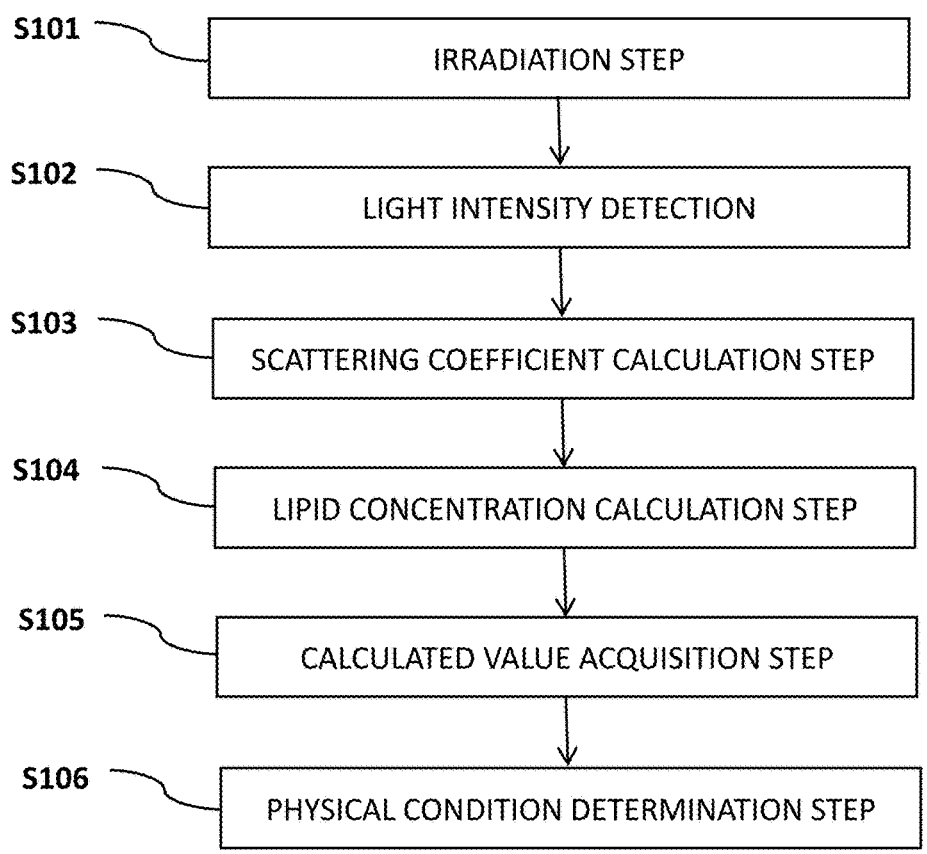
FIG. 4 is a flowchart of an operation method of the blood lipid concentration measurement device of the present embodiment.

Next, an operation method of the blood lipid concentration measurement device of the present embodiment will be described. FIG. 4 is a flowchart of the operation method of the blood lipid concentration measurement device of the present embodiment.

In an irradiation step (S101), continuous light is radiated to the irradiation position 21 using the irradiation portion 2. The light source 22 of the irradiation portion 2 preferably radiates light having a wavelength of 750 nm or more (a first wavelength) and irradiation light having a wavelength shorter than the first wavelength and of 900 nm or less (a second wavelength).

In a light intensity detection step (S102), the first light intensity detection portion 31 is used to detect a light intensity at the first detection position 331 and the second light intensity detection portion 32 is used to detect a light intensity at the second detection position 332. In the light intensity detection step, the irradiation light having the first wavelength emitted toward the outside of the living body from the living body is received to detect a first light intensity. In the light intensity detection step, the irradiation light having the second wavelength emitted toward the outside of the living body from the living body is received to detect a second light intensity. The light intensities detected at the first detection position 331 and the second detection position 332 are sent to a scattering coefficient calculation step.

Note that, in a case where a plurality of the detection positions 31 are arranged, a layout thereof is not limited to a linear form as long as they are arranged at different distances from the irradiation position 21 serving as a substantial center. The layout may be appropriately selected from a circular form, a wave form, a zigzag form, and the like. Further, the first radiation-detection distance ρ1 between the irradiation position 21 and the detection position 31, the second radiation-detection distance ρ2, and the interval between the detection positions 331 and 332 are not limited to certain intervals and they may be arranged continuously to each other.

In the scattering coefficient calculation step (S103), a light intensity difference or a light intensity ratio between the light intensity at the first detection position 331 and the light intensity at the second detection position 332 is calculated and then the scattering coefficient μs' is calculated on the basis of the light intensity difference or the light intensity ratio. In the scattering coefficient calculation step, a first scattering coefficient μs1' in the living body is calculated on the basis of the first light intensity detected in the light intensity detection step.

In the scattering coefficient calculation step, a second scattering coefficient μs2' in the living body is calculated on the basis of the second light intensity detected in the light intensity detection step. The first scattering coefficient μs1' and the second scattering coefficient μs2' thus calculated are sent to a lipid concentration calculation step.

In the lipid concentration calculation step (S104), a variation C2 of the blood concentration of the second lipid group including at least one type of lipids (for example, CM and a CM remnant) is calculated from a variation of the second scattering coefficient µs2'. Further, in the lipid concentration calculation step, a variation C1 of the blood concentration of the first lipid group including at least one type of lipids (for example, CM, a CM remnant, VLDL, and a VLDL remnant) whose particle diameter is equal to or less than that of the lipid included in the second lipid group is calculated from a variation of the first scattering coefficient µs1'.

In the lipid concentration calculation step (S104), a variation (C1-C2) of the concentration of the lipid that is not duplicated between the first lipid group and the second lipid group (for example, VLDL and a VLDL remnant) is calculated from the difference between the variation C1 of the concentration of the first lipid group and the variation C2 of the concentration of the second lipid group.

In a calculated value acquisition step (S105), the variation C1 of the concentration of the first lipid group, the variation C2 of the concentration of the second lipid group, and the difference therebetween (C1-C2) thus calculated are acquired via a communication line and sent to a physical condition determination step.

In the physical condition determination step (S106), a physical condition is determined on the basis of the variation C1 of the concentration of the first lipid group and the variation C2 of the concentration of the second lipid group. Determination of the physical condition is specifically described above and repeated description thereof is omitted. Further, in the physical condition determination step, a course of action to improve a lipid balance is determined from the variation (C1-C2) of the concentration of the lipid that is not duplicated between the first lipid group and the second lipid group.

As described above, according to the blood turbidity measurement device and the operation method thereof of the present embodiment, it becomes possible to perform a risk management of arteriosclerosis, a health management, and a dietary management by measuring the concentrations of the individual lipoproteins such as CM and VLDL.

It is conventionally believed that the measurement using light scattering measures the lipoproteins, CM and VLDL, and small fractions of LDL and HDL without any specificity of wavelength to CM, VLDL, or the like in the scattering. However, according to the evaluation performed by the present inventor, it is found that only CM (and CM-R) is measured by the irradiation light having a wavelength of 750 nm to 900 nm, or less. This feature makes it possible to selectively measure only CM (and CM-R) among a plurality of scattering bodies such as the skin, corpuscles, and tissues in the present embodiment. Further, in the present embodiment, utilizing such specificity allows the calculation of the concentration of VLDL (and VLDL-R) by subtracting the concentration of CM (and CM-R).

Second Embodiment

Note that, in the first embodiment described above, the description is given of the case where the lipid concentration is measured using the irradiation light having two different wavelengths. However, only the irradiation light having a wavelength of 900 nm or less may be used to measure the concentration of at least one of CM and a CM remnant.

A blood lipid concentration measurement device and an operation method thereof as a second embodiment of the present invention will be described below. Note that configurations of the blood lipid concentration measurement device and the operation method thereof as the second embodiment of the present invention are substantially the same as that of the blood lipid concentration measurement device and the operation method thereof of the first embodiment of the present invention, and thus the description will primarily focus on a part different from the first embodiment.

A blood lipid concentration measurement device 1 of the present embodiment includes: an irradiation portion 2 configured to radiate irradiation light toward a living body from an outside of the living body; a light intensity detection portion 3 configured to detect a light intensity at a predetermined detection position 31 outside the living body; a scattering coefficient calculation portion 4 configured to calculate a light scattering coefficient µs' in the living body on the basis of the light intensity detected by the light intensity detection portion 3; a lipid concentration calculation portion 5 configured to calculate a lipid concentration in the living body on the basis of the light scattering coefficient µs' calculated by the scattering coefficient calculation portion 4; and a physical condition management measurement device 10 configured to determine a physical condition on the basis of the lipid concentration.

The irradiation portion 2 includes a light source 22 for radiating the irradiation light to a predetermined irradiation position 21 toward an inside of the living body from the outside of the living body. The light source 22 of the present embodiment can adjust a wavelength of the irradiation light. The light source 22 of the present embodiment radiates the irradiation light having a wavelength of 900 nm or less.

The light intensity detection portion 3 receives the irradiation light emitted from the living body to the outside of the living body and detects the light intensity. In a case where a plurality of the light intensity detection portions 3 are used, the light intensity detection portions 3 are disposed at different distances from the irradiation position 21 serving as a substantial center.

In a case where a plurality of detection positions 31 are arranged, a layout thereof is not limited to a linear form as long as they are arranged at different distances from the irradiation position 21 serving as the substantial center. The layout may be appropriately selected from a circular form, a wave form, a zigzag form, and the like. Further, a first radiation-detection distance ρ1 between the irradiation position 21 and the detection position 31, a second radiation-detection distance ρ2, and an interval between detection positions 331 and 332 are not limited to certain intervals and they may be arranged continuously to each other.

The scattering coefficient calculation portion 4 calculates a scattering coefficient µs' in the living body on the basis of the light intensity detected by the light intensity detection portion 3.

The scattering coefficient calculation portion 4 in the present embodiment includes two calculation portions, a light intensity ratio calculation portion 42 and a light intensity difference calculation portion 43.

The light intensity ratio calculation portion 42 calculates the scattering coefficient µs' from a ratio between the light intensities detected by the plurality of light intensity detection portions 3. The light intensity ratio calculation portion 42 calculates the scattering coefficient µs' on the basis of a scattering phenomenon in which the radiated light is more attenuated by the scattering as the distance to a detection position 33 is increased.

The light intensity difference calculation portion 43 calculates the scattering coefficient µs' from a difference between the light intensities detected by the plurality of light intensity detection portions 3. As with the light intensity ratio calculation portion 42, the scattering coefficient µs' is calculated on the basis of the scattering phenomenon in which the radiated light is more attenuated by the scattering as the distance to the detection position 33 is increased.

The lipid concentration calculation portion 5 calculates a variation of a concentration of at least one of CM and a CM remnant from a variation of the scattering coefficient μs' calculated by the scattering coefficient calculation portion 4.

The physical condition management measurement device 10 determines a lipid metabolic state and a physical condition by acquiring the variation of the concentration of at least one of CM and a CM remnant calculated by the lipid concentration calculation portion 5. The physical condition management measurement device 10 of the present embodiment is connected to the lipid concentration calculation portion 5 via a communication line or the like. The physical condition management measurement device 10 includes a calculated-value acquisition portion 101 configured to acquire the lipid concentration calculated by the lipid concentration calculation portion 5 at predetermined time intervals and a physical condition determination portion 102 configured to determine the lipid metabolic state and the physical condition in accordance with a temporal change in the lipid concentration acquired by the calculated-value acquisition portion 101.

The physical condition determination portion 102 determines the physical condition of an examinee, for example, from a temporal change in the variation of the concentration of at least one of CM and a CM remnant acquired by the calculated-value acquisition portion 101.

The physical condition determination portion 102 determines a risk of arteriosclerosis from the temporal change in the concentration of at least one of CM and a CM remnant.

Next, an operation method of the blood lipid concentration measurement device of the present embodiment will be described.

In an irradiation step (S201), continuous light is radiated to the irradiation position 21 using the irradiation portion 2. A light source 22 of the irradiation portion 2 radiates irradiation light having a wavelength of 900 nm or less.

In a light intensity detection step (S202), the first light intensity detection portion 31 is used to detect a light intensity at the first detection position 331 and the second light intensity detection portion 32 is used to detect a light intensity at the second detection position 332. In the light intensity detection step, the irradiation light having the wavelength of 900 nm or less emitted toward the outside of the living body from the living body is received to detect the light intensity. The light intensities detected at the first detection position 331 and the second detection position 332 are sent to a scattering coefficient calculation step.

In the scattering coefficient calculation step (S203), a light intensity difference or a light intensity ratio between the light intensity at the first detection position 331 and the light intensity at the second detection position 332 is calculated and then the scattering coefficient μs' is calculated on the basis of the light intensity difference or the light intensity ratio. The scattering coefficient μs' thus calculated is sent to a lipid concentration calculation step.

In the lipid concentration calculation step (S204), the variation of the concentration of at least one of CM and a CM remnant is calculated from the variation of the scattering coefficient μs'.

In a calculated value acquisition step (S205), the variation of the concentration of at least one of CM and a CM remnant thus calculated is acquired via a communication line and sent to a physical condition determination step.

In the physical condition determination step (S206), a physical condition is determined on the basis of the variation of the concentration of at least one of CM and a CM remnant. Determination of the physical condition is specifically described above and repeated description thereof is omitted.

As described above, in the present embodiment, it becomes possible to calculate the variation of the concentration of at least one of CM and a CM remnant by using the irradiation light having a wavelength of 900 nm or less. This allows determination of the physical condition on the basis of the variation of the concentration of at least one of CM and a CM remnant. Further, a risk of arteriosclerosis can be determined from a temporal change in the concentration of at least one of CM and a CM remnant.

Third Embodiment

A blood lipid concentration measurement device of a third embodiment of the present invention will be described below. Note that a configuration of the blood lipid concentration measurement device as the third embodiment of the present invention is partially overlapped with that of the blood lipid concentration measurement devices of the first and second embodiments of the present invention, and thus the description will primarily focus on a part different from the first and second embodiments.

In the first and second embodiments described above, the configuration example in which the irradiation portion 2, the light intensity detection portion 3, the scattering coefficient calculation portion 4, the lipid concentration calculation portion 5, and the physical condition management measurement device 10 are integrally formed and the configuration example in which the irradiation portion 2, the light intensity detection portion 3, the scattering coefficient calculation portion 4, the lipid concentration calculation portion 5, and the physical condition management measuring portion 10 are separately formed are shown. However, the present invention is not limited to these examples and may provide a system in which a user device is configured from the irradiation portion 2 configured to radiate light and the light intensity detection portion 3 and a blood lipid concentration measurement device is configured from the scattering coefficient calculation portion 4, the lipid concentration calculation portion 5, the calculated value acquisition portion 101, and the physical condition determination portion 102.

Figure 14:
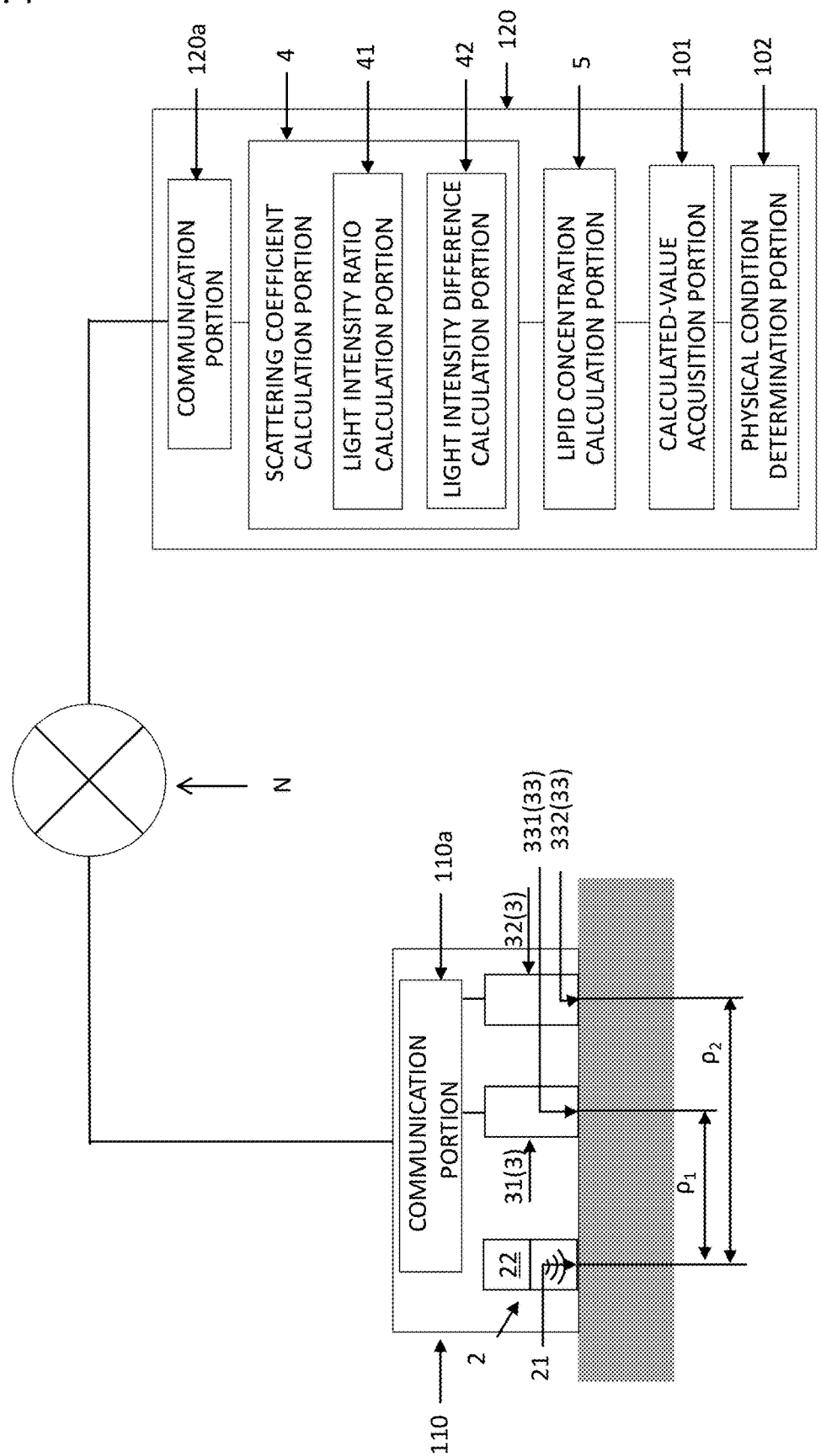
FIG. 14 is a block diagram illustrating a configuration of a blood lipid concentration measurement system of the present embodiment.

FIG. 14 is a block diagram illustrating a configuration of a blood lipid concentration measurement system of the present embodiment. A user device 110 and a blood lipid concentration measurement device 120 of the present embodiment, used for measuring the blood lipid concentration, each include a CPU (arithmetic unit) and a memory device (storage unit such as a RAM and a ROM) and functions as a device shown in the block diagram in FIG. 14 by executing a program stored in the memory device.

A blood lipid concentration measurement system 100 of the present embodiment is configured from the user device 110 configured to measure a light intensity and the blood lipid concentration measurement device 120 configured to calculate a lipid concentration from the light intensity. The user device 110 and the blood lipid concentration measurement device 120 are connected to a network via a wireless or wired communication network N.

The blood lipid concentration measurement device 120 is a device configured to perform a predetermined process on the basis of the light intensity sent from the user device 110 and calculate a lipid concentration. Specifically, a personal computer or a server apparatus, depending on the number of devices and an amount of data to be transmitted and received, may be appropriately used.

The user device 110 is a device that is carried by a user. The user device 110 may be a dedicated device or installed in a cellular phone, a wristwatch, or the like.

The user device 110 includes an irradiation portion 2 configured to radiate light, a light intensity detection portion 3, and a communication portion 110a. The communication portion 110a sends a light intensity detected by the light intensity detection portion 3. The operations and functions of the irradiation portion 2 and the light intensity detection portion 3 are the same as those in the first embodiment and the second embodiment described above.

The blood lipid concentration measurement device 120 includes a communication portion 120a, a scattering coefficient calculation portion 4, a lipid concentration calculation portions, a calculated value acquisition portion 101, and a physical condition determination portion 102. The communication portion 120a receives the light intensity sent from the communication portion 110a via a wired or wireless network N and sends it to the scattering coefficient calculation portion 4. The operations and functions of the scattering coefficient calculation portion 4, the lipid concentration calculation portion 5, the calculated value acquisition portion 101, and the physical condition determination portion 102 are the same as those in the first embodiment and the second embodiment described above.

Note that, in the present embodiment, the light intensity is sent from the user device 110 to the blood lipid concentration measurement device 120 via the network N. However, the present invention is not limited thereto, and the user device 110 may be directly connected to the blood lipid concentration measurement device 120 without using the network N and send the light intensity by a means such as a wired communication and a wireless communication.

The blood lipid concentration measurement device of the present embodiment is communicatively connected to a user device that includes: an irradiation portion configured to radiate irradiation light having a first wavelength and irradiation light having a second wavelength shorter than the first wave length at predetermined light intensities toward an inside of a living body from an outside of the living body; a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion; and a communication portion configured to send the first light intensity and the second light intensity detected by the light intensity detection portion, the blood lipid concentration measurement device including: a scattering coefficient calculation portion configured to calculate a first scattering coefficient and a second scattering coefficient in the living body on the basis of the first light intensity and the second light intensity sent from the user device; and a lipid concentration calculation portion configured to calculate a variation of a concentration of a second lipid group in the blood on the basis of a variation of the second scattering coefficient and calculate a variation of a concentration of a first lipid group including a lipid whose particle diameter is equal to or less than that of a lipid included in the second lipid group on the basis of a variation of the first scattering coefficient.

Further, the lipid concentration calculation portion of the blood lipid concentration measurement device of the present embodiment calculates a variation of a concentration of the lipid that is not duplicated between the first lipid group and the second lipid group from a difference between the variation of the concentration of the first lipid group and the variation of the concentration of the second lipid group.

Further, the blood lipid concentration measurement device of the present embodiment further includes a physical condition determination portion configured to determine a physical condition on the basis of the variation of the concentration of the first lipid group and the variation of the concentration of the second lipid group.

Further, in the blood lipid concentration measurement device of the present embodiment, the first wavelength is 750 nm or more and the second wavelength is shorter than the first wavelength and 900 nm or less.

Further, in the blood lipid concentration measurement device of the present embodiment, the first lipid group includes at least one of CM and a CM remnant and at least one of VLDL and a VLDL remnant, and the second lipid group includes at least one of CM and a CM remnant.

Further, in the blood lipid concentration measurement device of the present embodiment, an irradiation position and a detection position at which the light intensity is detected are arranged apart from each other by a predetermined radiation-detection distance, and the light intensity detection portion detects the light intensity of back scattered light scattered by a lipid in the blood.

Further, in the blood lipid concentration measurement device of the present embodiment, the irradiation portion is a light source that emits continuous light, the light source radiates light, a plurality of the light intensity detection portions disposed at different distances from the irradiation position serving as a substantial center detect light intensities at respective detection positions, and the scattering coefficient calculation portion calculates a light scattering coefficient in the living body on the basis of a ratio or difference between the respective light intensities detected by the respective light intensity detection portions.

Further, the physical condition determination portion of the blood lipid concentration measurement device of the present embodiment determines a total absorption amount of alcohol or fats from a temporal change in a concentration of at least one of VLDL and a VLDL remnant.

Further, the physical condition determination portion of the blood lipid concentration measurement device of the present embodiment determines a risk of arteriosclerosis from a temporal change in a concentration of at least one of CM and a CM remnant.

Further, the physical condition determination portion of the blood lipid concentration measurement device of the present embodiment determines a course of action to improve a lipid balance from a difference between the variation of the concentration of the first lipid group and the variation of the concentration of the second lipid group.

Further, the blood lipid concentration measurement device of the present embodiment is communicatively connected to a user device that includes: an irradiation portion configured to radiate irradiation light having a wavelength of 900 nm or less at a predetermined light intensity toward an inside of a living body from an outside of the living body; a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion; and a communication portion configured to send the light intensity detected by the light intensity detection portion, the blood lipid concentration measurement device including: a scattering coefficient calculation portion configured to calculate a scattering coefficient in the living body on the basis of the light intensity sent from the user device; and a lipid concentration calculation portion configured to calculate a variation of only a concentration of at least one of CM and a CM remnant in the blood on the basis of a variation of the scattering coefficient.

Further, the blood lipid concentration measurement device of the present embodiment further includes a physical condition determination portion configured to determine a physical condition on the basis of the variation of the concentration of at least one of CM and a CM remnant.

Further, the physical condition determination portion in the blood lipid concentration measurement device of the present embodiment determines a risk of arteriosclerosis from a temporal change in the concentration of at least one of CM and a CM remnant.

EXAMPLES

Hereinafter, examples of the present invention will be described; however, the present invention is not limited to the following examples.

Figure 5:
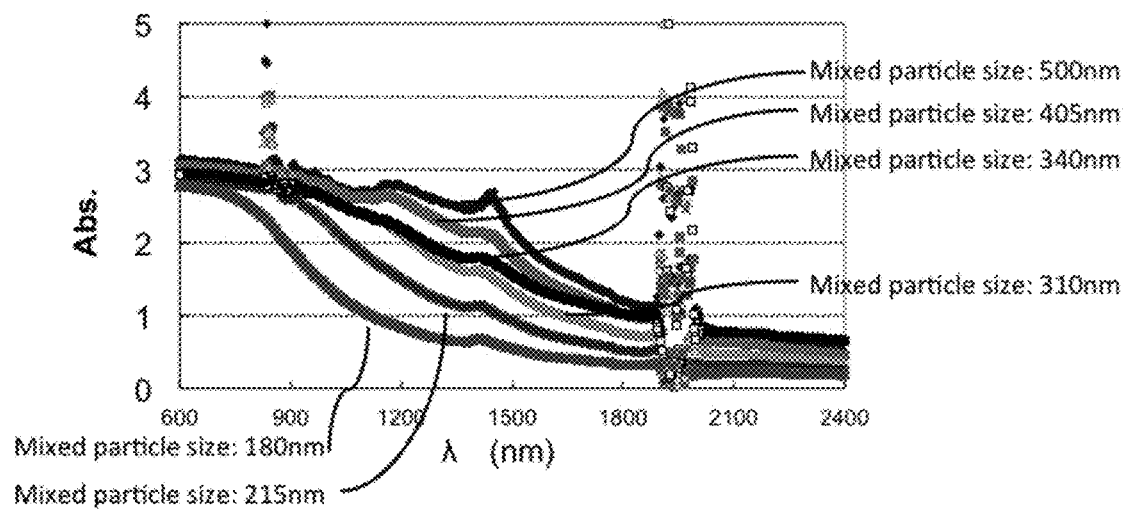
FIG. 5 is a diagram illustrating a result of measuring samples prepared by mixing standard latex in predetermined ratios with a spectrophotometer.

FIG. 5 is a diagram illustrating a result of measuring samples prepared by mixing standard latex in predetermined ratios with a spectrophotometer. Since latex particles area measurement object, absorbance shown in a vertical axis of the graph represents an apparent absorbance obtained by actually measuring turbidity (also referred to as a scattering intensity). Particle diameters of the latex used herein are 25, 50, 100, 200, and 500 nm.

As shown in FIG. 5, the samples prepared by mixing the latex particles of arbitrary particle diameters (hereinafter referred to as latex mixing samples) are compared for their spectra to find that scattering intensities tend to converge on a shorter wavelength side (800 nm or less) and a longer wavelength side (1,900 nm or more) of the irradiation light. As shown in FIG. 5, the wavelengths of the irradiation light between 800 nm and 1,900 nm constitute a wavelength range where the scattering intensities obtained from various latex mixing ratios do not overlap each other. This indicates that a high resolution is obtained with the irradiation light having the wavelength between 900 nm and 1,800 nm.

Figure 6:
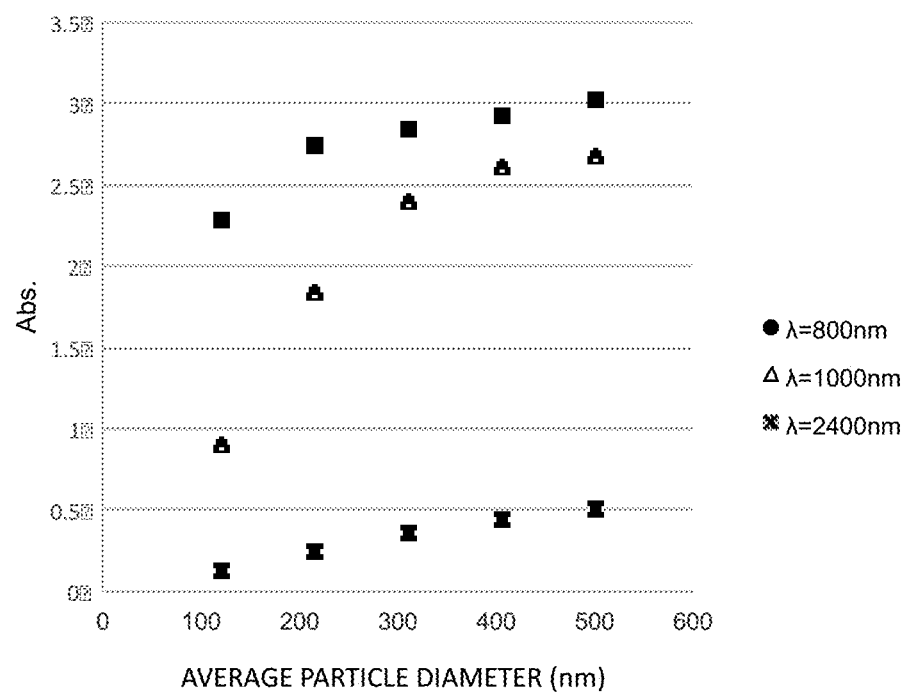
FIG. 6 is a diagram illustrating a result of measuring absorbance of the latex mixing samples with respect to average particle diameters of latex particles.

After finding that a high resolution is obtained with the irradiation light having the wavelength between 900 nm and 1,800 nm, the wavelength suitable for measuring an average particle diameter of lipids was examined. FIG. 6 is a diagram illustrating a result of measuring the absorbance (the scattering intensities) of the latex mixing samples obtained with respect to the average particle diameters of the latex particles using three wavelengths of the irradiation light, 800 nm, 1,000 nm, and 2,400 nm. As shown in FIG. 6, linearity is substantially obtained until the average particle diameter of the latex particles reaches 300 nm in each wavelength range. As shown in FIG. 6, a high resolution is found around 1,000 nm in the wavelength of the irradiation light. In FIG. 6, it can be confirmed that linearity of the absorbance (the scattering intensity) is obtained with the irradiation light having the wavelength of 2,400 nm.

The scattering intensity depends on two factors, a size (a particle diameter) and the number (the particle number) of scattering bodies. In particular, the scattering intensity is known to be dependent on the particle diameter, and it is understood that the scattering intensity is proportional to the cube of the particle diameter. Since a large particle has a huge influence, the scattering intensity is largely dependent on a concentration of the large particles, thus the measurement of the scattering intensity easily reaches a plateau in the presence of the large particles. However, in a case where the irradiation light having a long side of wavelength (for example, 2,400 nm) is used, a linearity relation between the average particle diameter and the scattering intensity is obtained independent of the concentration of the large particles in the mixed latex. Thus, the scattering intensity is considered to measure the average particle diameter of the latex particles.

Figure 7:
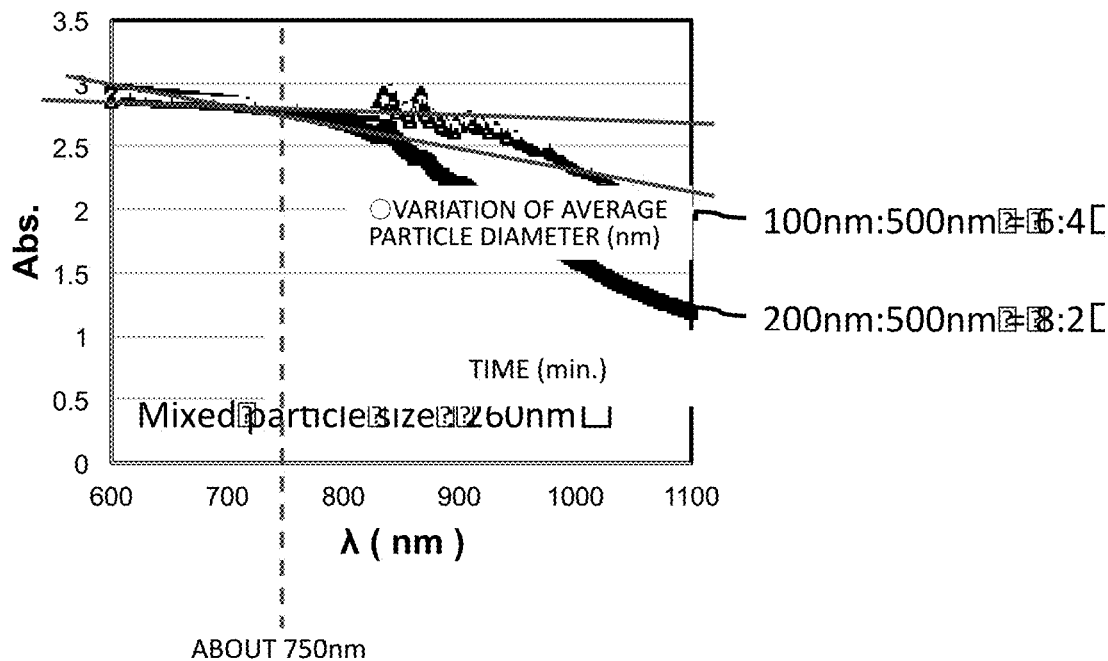
FIG. 7 is a diagram illustrating a result of measuring absorbance of the latex mixing samples, which have the same average particle diameter but contain latex particles of different particle diameters in different mixing ratios.
Figure 8:
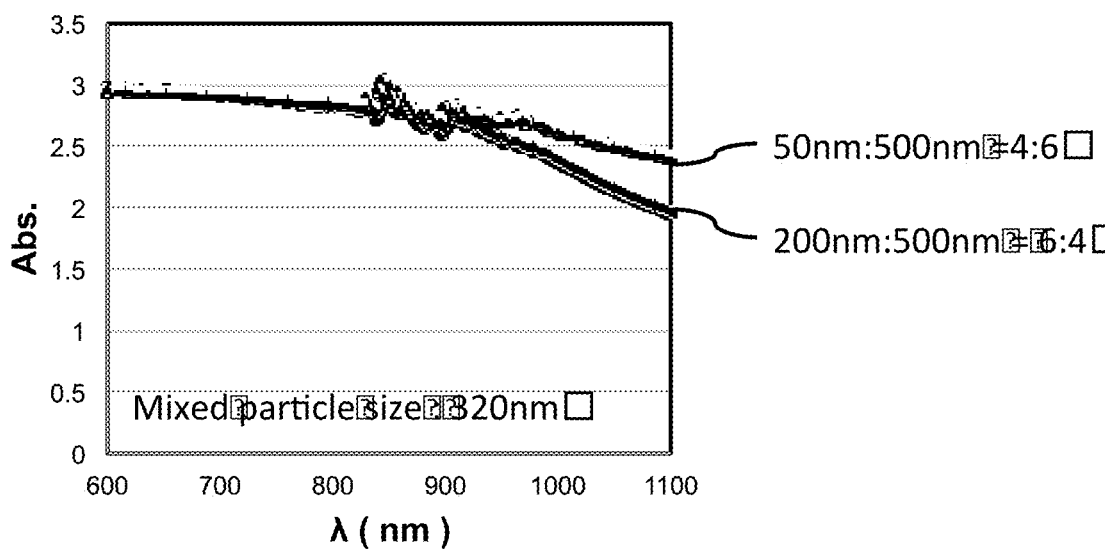
FIG. 8 is a diagram illustrating a result of measuring absorbance of the latex mixing samples, which have the same average particle diameter but contain latex particles of different particle diameters in different mixing ratios.

FIGS. 7 and 8 are diagrams illustrating results of measuring the absorbance (the scattering intensities) of the latex mixing samples which have the same average particle diameters of the latex particles in the latex mixing samples but contain the latex particles of different particle diameters indifferent mixing ratios. As shown in FIGS. 7 and 8, the absorbance (the scattering intensities) with respect to the wavelength of the irradiation light varies between the latex mixing samples having different mixing ratios of the large particles and the small particles of the latex particles despite having the same average particle diameters of the latex particles.

Further, in a case of the average particle diameter of 260 nm, the latex mixing ratio is set as follows: particle diameter 200 nm:particle diameter 500 nm=8:2; particle diameter 100 nm:particle diameter 500 nm=6:4. Further, in a case of the average particle diameter of 320 nm, the latex mixing ratio is set to as follows: particle diameter 200 nm:particle diameter 500 nm=6:4; particle diameter 50 nm:particle diameter 500 nm=4:6.

Here, the particle diameters of 500 nm and 200 nm assume the particle diameter of CM, while the particle diameters of 100 nm and 50 nm assume the particle diameter of VLDL. Two sizes are prepared to assume their corresponding remnants. Further, CM and VLDL are assumed because a change in the scattering observed in postprandial hyperlipidemia is caused by CM and VLDL.

As shown in FIG. 7 and FIG. 8, when the latex mixing samples have the same average particle diameters of the latex particles, the absorbances are almost identical to each other with the irradiation light having a short side of wavelength of 750 nm or less, but differs from each other with the irradiation light having a longer side of wavelength than 750 nm. That is, the influence of the large particles of the latex particles on the scattering intensity becomes relatively weak and the influence of the small particles of the latex particles on the scattering intensity becomes relatively strong with the irradiation light having a longer side of wavelength than 750 nm.

Such a phenomenon can be interpreted to suggest the existence of a wavelength of the irradiation light that serves as a boundary for determining the influence on the scattering intensity. That is, it is speculated that the phenomenon is explained by a difference between equal scattering in which scattering occurs equally in all 360-degree directions of the lipid particle and Mie scattering in which scattering occurs intensely in a light traveling direction. That is, under such a phenomenon, an object is turbid but appears bright with the irradiation light having a long wavelength.

In the present tests, the average particle diameters of the latex particles are kept constant, and thus the scattering intensity is determined by two factors, the particle diameter of the latex particles and the wavelength of the irradiation light. In general, when the wavelength of the irradiation light is short, a distance between two successive crests becomes short, thereby increasing the probability of collision of the light with a scattering body such as the latex particle and increasing the scattering intensity. Further, when the particle diameter of the latex particles is large, the probability of collision of the light with the latex particle similarly increases and thus the scattering intensity also increases.

As shown in FIG. 6, when the irradiation light having a short side of wavelength (for example, 800 nm) is used, the scattering intensity becomes strong. Further, as shown in FIG. 6, as the wavelength of the irradiation light becomes shorter, the scattering intensity reaches a measurement upper limit even though the average particle diameter of the latex particles is relatively small (for example, 100 nm). Thus, the influence of the average particle diameter of the latex particles becomes larger. Note that, in the present tests, the latex mixing samples include the latex particles having relatively large particle diameters. That is, it can be understood that the irradiation light having a short side of wavelength hardly passes through gaps between the large latex particles.

On the other hand, when the irradiation light having a long side of wavelength (for example, around 2,400 nm) is used, the influence of the average particle diameter of the latex particles on the scattering intensity is small. Further, the linearity is obtained with the irradiation light having a long wavelength, indicating that the irradiation light having a long side of wavelength can easily pass through the gaps between the latex particles of relatively large particle diameters. Further, obtaining the linearity of the scattering intensity indicates that scattering of the small particles of the latex particles existing in the gaps between the large particles of the latex particles can be detected by using the irradiation light having a long wavelength.

On the other hand, there are a number of large particles called red corpuscles whose particle diameter is about 5,000 nm in the blood. It is speculated that the particle diameter of the lipoprotein is at most 1,000 nm, thus the lipoprotein having the particle diameter of 200 nm is considered as a small particle.

Figure 9A:
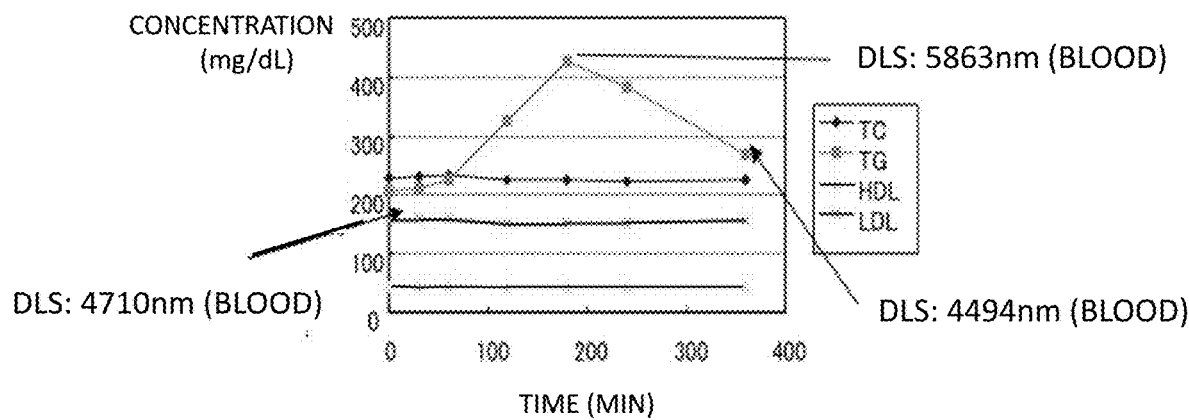
FIG. 9A is a diagram illustrating a result of measuring a change in the average particle diameter of the blood using DLS during a fat loading test.

FIG. 9A is a diagram illustrating a result of measuring a change in the average particle diameter of the blood during a fat loading test using dynamic light scattering (DLS). As shown in FIG. 9A, it was confirmed that the average particle diameter of the blood increased in a concentration region where a lipid concentration reached maximum. Further, it was confirmed that the average particle diameter returned to its original state 6 hours after the fat loading test. "DLS: 4710 nm, 5863 nm, 4464 nm" in the drawing represents the particle diameter of the blood (all blood components including corpuscles and lipoproteins) which is measured in the collected whole blood using dynamic light scattering (DLS).

Figure 9B:
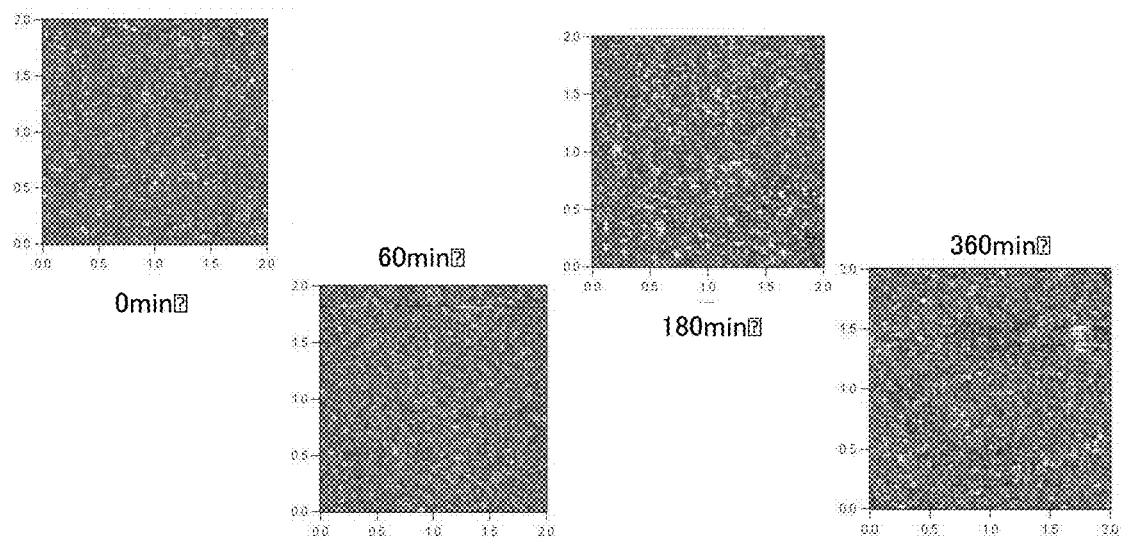
FIG. 9B is a diagram demonstrating the existence of large particles of lipids in the serum using AFM.

However, as shown in FIG. 9B, observation of the serum with an atomic force microscopy (AFM) confirmed the presence of the large lipid particles even 6 hours after the fat loading test.

That is, it was found that a turbid intensity of the blood after eating was in two states: a high lipid state in which there were a number of large particles such as CM, so that the average particle diameter of the blood including corpuscles increased; and a lipid state in which a smaller number of the large particles such as CM existed at a level which did not cause a significant influence on the average particle diameter of the blood in the measurement.

Here, the particle diameters of the corpuscles are sufficiently larger than the wavelength of the irradiation light, and thus the scattering caused by the corpuscles is similar to the one caused by mirror face reflection and has a little influence on the scattering intensities obtained by different wavelengths of the irradiation light. On the other hand, the lipid particles have the particle diameters that significantly influence the scattering intensities obtained by different wavelengths of the irradiation light.

Thus, for measuring a turbid state in which the average particle diameter of the blood is influenced by having a number of the large lipid particles such as CM, the scattering intensity can be measured with higher sensitivity using the irradiation light having a short side of wavelength as is the case with a general scattering measurement. Such scattering measurement is used to examine, for example, a peak time during the fat loading test.

On the other hand, for measuring a changing range of an optical property such as a light traveling direction dependency in Mie scattering, observation is preferably performed using the irradiation light having a wavelength longer than the range of 750 nm to 900 nm. That is, such scattering measurement is used in a state where scattering bodies accumulate in the blood without causing turbidity that significantly influences the average particle diameter of the blood.

Therefore, for measuring the scattering caused by the lipids in the blood, a range of 750 nm to 900 nm constitutes a so-called gray zone as seen in FIGS. 7 and 8. However, at least, it can be said that the scattering intensity of the large particles is suitably measured with the irradiation light having a short side of wavelength of 900 nm or less and the scattering intensity of the small particles is suitably measured with the irradiation light having a long side of wavelength of 750 nm or more. As such, when the measurement is performed using two wavelengths, the first wavelength is preferably set to 750 nm or more and the second wavelength is preferably set to be shorter than the first wavelength and 900 nm or less. Further, for measuring at least one of CM and a CM remnant, which are relatively large particles, the wavelength of the irradiation light is preferably set to 900 nm or less.

Figure 10:
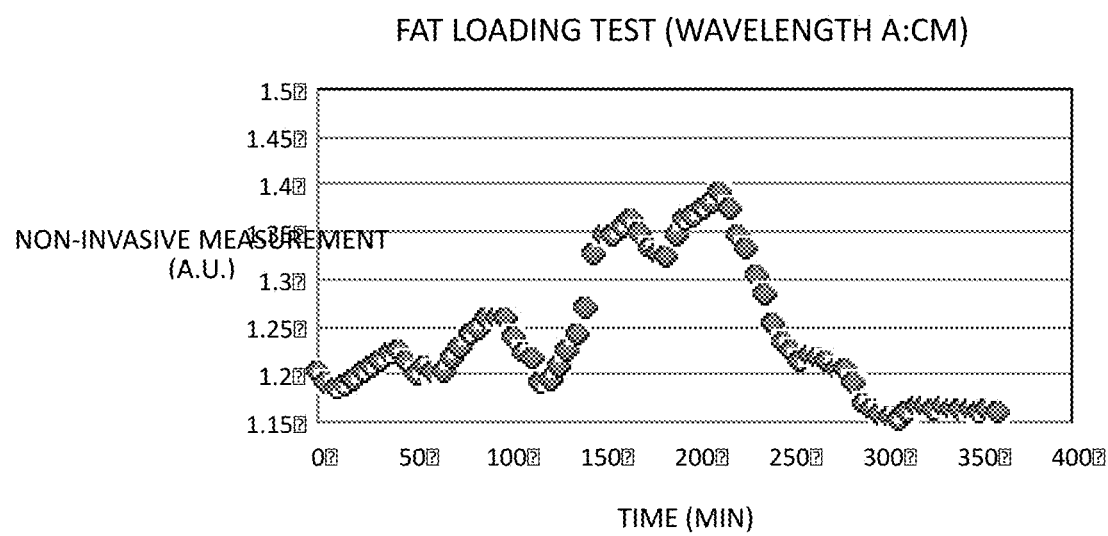
FIG. 10 is a diagram illustrating a result of performing the fat loading test using irradiation light having a short wavelength.
Figure 11:
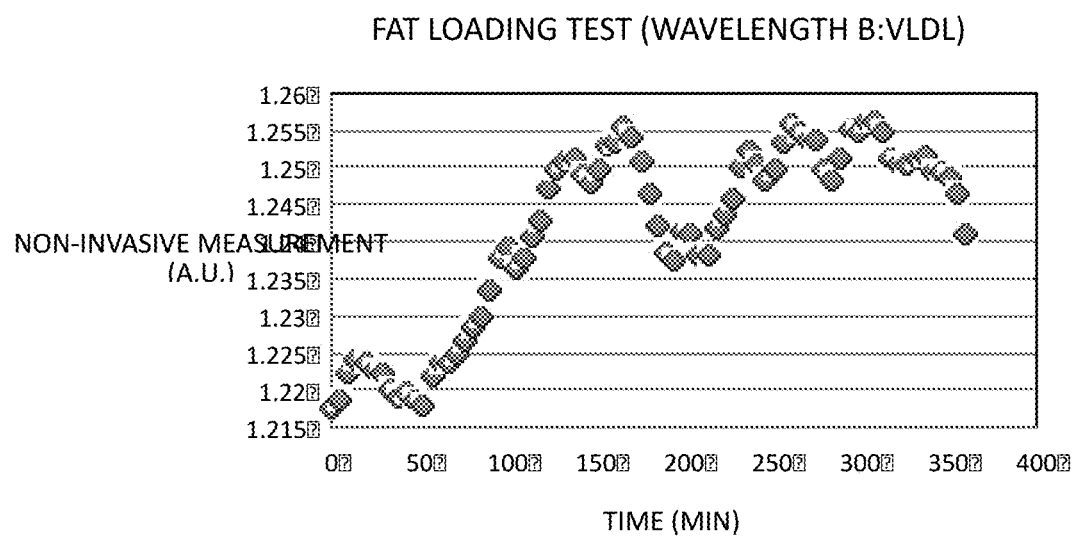
FIG. 11 is a diagram illustrating a result of performing the fat loading test using irradiation light having a long wavelength.
Figure 12:
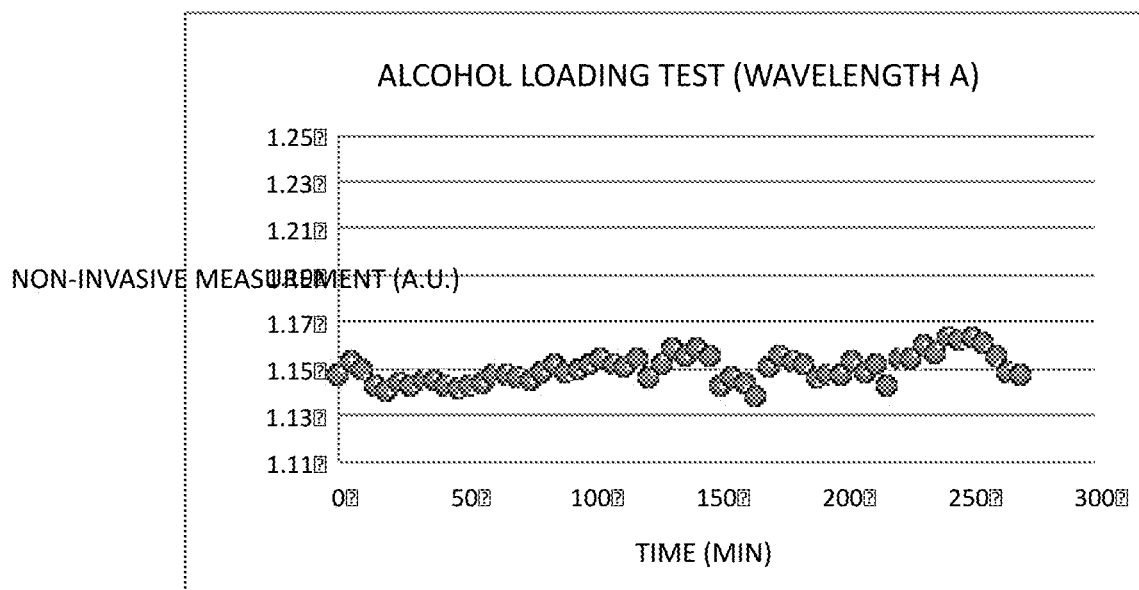
FIG. 12 is a diagram illustrating a result of performing an alcohol loading test using irradiation light having a short wavelength.
Figure 13:
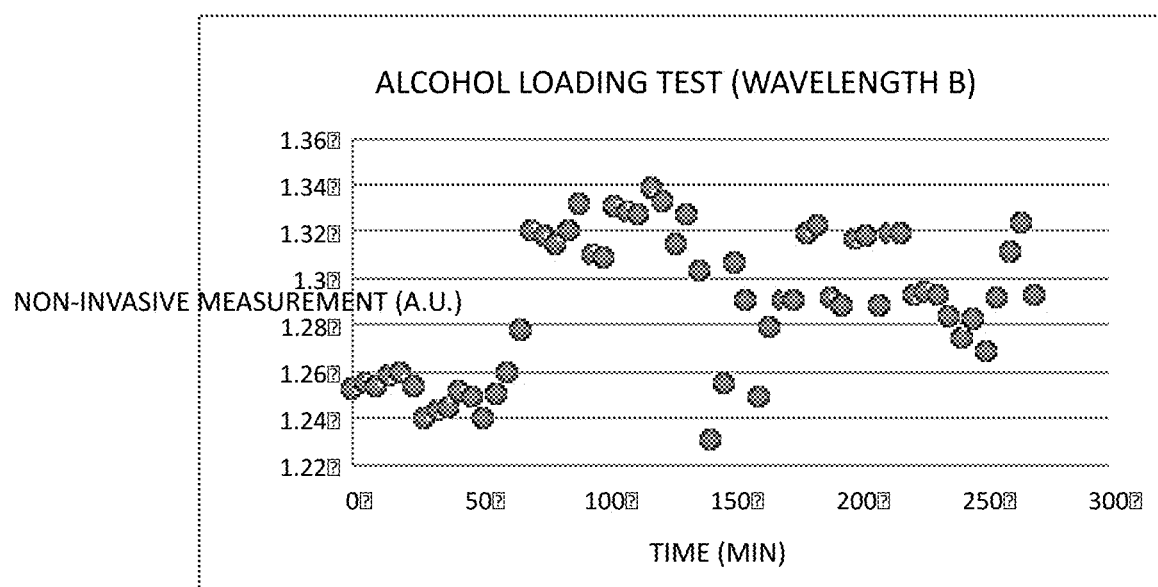
FIG. 13 is a diagram illustrating a result of performing the alcohol loading test using irradiation light having a long wavelength.

The present inventor performed the fat loading test and alcohol loading test to validate the adequacy of setting the boundary of the wavelength of the irradiation light between 750 nm and 900 nm. FIG. 10 is a diagram illustrating a result of performing the fat loading test using the irradiation light having a short wavelength. FIG. 11 is a diagram illustrating a result of performing the fat loading test using the irradiation light having a long wavelength. FIG. 12 is a diagram illustrating a result of performing the alcohol loading test using the irradiation light having a short wavelength. FIG. 13 is a diagram illustrating a result of performing the alcohol loading test using the irradiation light having a long wavelength. Note that the short wavelength was set to 810 nm and the long wavelength was set to 970 nm in the present evaluation.

In both the fat loading test and the alcohol loading test, studies were conducted with male subjects in their 40s. In the fat loading test, the male subjects were asked to fast after 21:00 the day before the test and start the test by ingesting 160 g of OFTT cream (manufactured by Jyoumou Corp.) at 9:00 next morning. Non-invasive measurement of a variation of the scattering coefficient (vertical axes in FIGS. 10 and 11) was continued for 6 hours (horizontal axes in FIGS. 10 and 11) after the ingestion.

Similarly, in the alcohol loading test, the male subjects were asked to fast after 21:00 the day before the test and start the test by ingesting alcohol at 9:00 next morning. The male subjects took 2 hours to ingest a commercially available Japanese distilled liquor, shochu, as alcohol with hot water while considering an effect of sugar. The amount of shochu was about 350 ml. A variation of the scattering coefficient (vertical axes in FIGS. 12 and 13) was measured for 4.5 hours (horizontal axes in FIGS. 12 and 13) after the ingestion.

As shown in FIGS. 10 and 11, in the fat loading test, an increase in the variation of the scattering coefficient (i.e., an increase in the variation of the lipid concentration) and a similar pattern of the scattering coefficient by the non-invasive measurement can be confirmed using both the irradiation light having the short side of wavelength (FIG. 10) and the irradiation light having the long side of wavelength (FIG. 11).

On the other hand, as shown in FIGS. 12 and 13, no change is confirmed using the irradiation light having the short side of wavelength (FIG. 12) and the irradiation light having the long side of wavelength (FIG. 13) in the alcohol loading test.

This is because the irradiation light having the short side of wavelength measures the CM particles that are the largest particles among the lipid particles. A mechanism by which a blood triglyceride concentration is increased by alcohol is as follows: alcohol is absorbed as it is and metabolized in the liver. The alcohol is then secreted from the liver as VLDL. In the alcohol loading test in FIGS. 12 and 13, the CM particles are not generated, and thus a measurement value of the variation of the scattering intensity does not change when using the irradiation light having the short side of wavelength as shown in FIG. 12. On the other hand, as shown in FIG. 13, a measurement value of the variation of the scattering intensity changes when using the irradiation light having the long side of wavelength, as such irradiation light measures the VLDL particles which are smaller than the CM particles.

The results shown in FIGS. 10 to 13 prove the adequacy of setting the boundary of the wavelength of the irradiation light at around 900 nm. That is, it can be concluded that CM exhibits the scattering intensity strong enough to increase the average particle diameter of the blood, while VLDL exhibits the scattering intensity not strong enough to influence the average particle diameter of the blood.

As described above, the blood lipid concentration measurement device of the first embodiment of present invention includes: an irradiation portion configured to irradiate irradiation light having a first wavelength and irradiation light having a second wavelength shorter than the first wavelength at predetermined light intensities toward an inside of a living body from an outside of the living body; a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion; a scattering coefficient calculation portion configured to calculate a first scattering coefficient and a second scattering coefficient in the living body respectively on the basis of the first light intensity and the second light intensity detected by the light intensity detection portion; and a lipid concentration calculation portion configured to calculate a variation of a concentration of a second lipid group in the blood on the basis of a variation of the second scattering coefficient and calculate a variation of a concentration of a first lipid group including a lipid whose particle diameter is equal to or less than that of a lipid included in the second lipid group on the basis of a variation of the first scattering coefficient.

The lipid concentration calculation portion calculates a variation of a concentration of the lipid that is not duplicated between the first lipid group and the second lipid group from a difference between the variation of the concentration of the first lipid group and the variation of the concentration of the second lipid group.

The blood lipid concentration measurement device further includes a physical condition determination portion configured to determine a physical condition on the basis of the variation of the concentration of the first lipid group and the variation of the concentration of the second lipid group.

The first wavelength is 750 nm or more and the second wavelength is shorter than the first wavelength and 900 nm or less.

The first lipid group includes at least one of CM and a CM remnant and at least one of VLDL and a VLDL remnant, and the second lipid group includes at least one of CM and a CM remnant.

The irradiation position and a detection position at which the light intensity is detected are arranged apart from each other by a predetermined radiation-detection distance, and the light intensity detection portion detects the light intensity of back scattered light scattered by a lipid in the blood.

The irradiation portion is a light source that emits continuous light, the light source radiates light, a plurality of the light intensity detection portions disposed at different distances from the irradiation position serving as a substantial center detect light intensities at respective detection positions, and the scattering coefficient calculation portion calculates a light scattering coefficient in the living body on the basis of a ratio or difference between the respective light intensities detected by the respective light intensity detection portions.

The physical condition determination portion determines a total absorption amount of alcohol or fats from a temporal change in a concentration of the at least one of VLDL and a VLDL remnant.

The physical condition determination portion determines a risk of arteriosclerosis from a temporal change in the concentration of the at least one of CM and a CM remnant.

The physical condition determination portion determines a course of action to improve a lipid balance from a difference between the variation of the concentration of the first lipid group and the variation of the concentration of the second lipid group.

Furthermore, the blood lipid concentration measurement device of the embodiment of the present invention includes: an irradiation portion configured to radiate irradiation light having a wavelength of 900 nm or less at a predetermined light intensity toward an inside of a living body from an outside of the living body; a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion; a scattering coefficient calculation portion configured to calculate a scattering coefficient in the living body on the basis of the light intensity detected by the light intensity detection portion; and a lipid concentration calculation portion configured to calculate a variation of a concentration of at least one of CM and a CM remnant in the blood on the basis of a variation of the scattering coefficient.

The blood lipid concentration measurement device of the present embodiment further includes a physical condition determination portion configured to determine a physical condition on the basis of the variation of the concentration of the at least one of CM and a CM remnant.

The physical condition determination portion determines a risk of arteriosclerosis from a temporal change in the concentration of the at least one of CM and a CM remnant.

The method for operating a blood lipid concentration measurement device of the embodiment of the present invention includes: an irradiation step of radiating irradiation light having a first wavelength and irradiation light having a second wavelength shorter than the first wavelength at predetermined light intensities toward an inside of a living body from an outside of the living body; a light intensity detection step of detecting an intensity of first light and an intensity of second light both emitted from the living body to measure a radiation-detection distance dependent attenuation of light intensities of the radiated irradiation light having the first wavelength and the radiated irradiation light having the second wavelength at a position with a predetermined interval from or continuously to a light irradiation position in the irradiation step; a scattering coefficient calculation step of calculating a first scattering coefficient and a second scattering coefficient in the living body respectively on the basis of the first light intensity and the second light intensity detected in the light intensity detection step; and a lipid concentration calculation step of calculating a variation of a concentration of a second lipid group in the blood on the basis of a variation of the second scattering coefficient and calculating a variation of a concentration of a first lipid group including a lipid whose particle diameter is equal to or less than that of a lipid included in the second lipid group on the basis of a variation of the first scattering coefficient.

In the lipid concentration calculation step, a variation of a concentration of a lipid that is not duplicated between the first lipid group and the second lipid group is calculated from a difference between the variation of the concentration of the first lipid group and the variation of the concentration of the second lipid group.

The method for operating a blood lipid concentration measurement device of the embodiment of the present invention further includes a physical condition determination step of determining a physical condition on the basis of the variation of the concentration of the first lipid group and the variation of the concentration of the second lipid group.

The first wavelength is 750 nm or more and the second wavelength is shorter than the first wavelength and 900 nm or less.

The first lipid group includes at least one of CM and a CM remnant and at least one of VLDL and a VLDL remnant, and the second lipid group includes at least one of CM and a CM remnant.

The irradiation position and a detection position at which the light intensity is detected are arranged apart from each other by a predetermined radiation-detection distance, and in the light intensity detection step, the light intensity of back scattered light scattered by a lipid in the blood is detected.

In the irradiation step, continuous light is radiated. In the light intensity detection step, the light intensities at a plurality of detection positions arranged at different distances from the irradiation position of the radiated light serving as a substantial center are detected. In the scattering coefficient calculation step, alight scattering coefficient in the living body is calculated on the basis of a ratio or difference between the respective light intensities detected at the plurality of detection positions.

In the physical condition determination step, a total absorption amount of alcohol or fats is determined from a temporal change in the concentration of the at least one of VLDL and a VLDL remnant.

In the physical condition determination step, a risk of arteriosclerosis is determined from a temporal change in the concentration of the at least one of CM and a CM remnant.

In the physical condition determination step, a course of action to improve a lipid balance is determined from a difference between the variation of the concentration of the first lipid group and the variation of the concentration of the second lipid group.

The method for operating a blood lipid concentration measurement device of the embodiment of the present invention includes: an irradiation step of radiating irradiation light having a wavelength of 900 nm or less at a predetermined light intensity toward an inside of a living body from an outside of the living body; a light intensity detection step of detecting an intensity of light emitted from the living body to measure a radiation-detection distance dependent attenuation of a light intensity of the radiated irradiation light at a position with a predetermined interval from or continuously to a light irradiation position in the irradiation step; a scattering coefficient calculation step of calculating a scattering coefficient in the living body on the basis of the light intensity detected in the light intensity detection step; and a lipid concentration calculation step of calculating a variation of a concentration of at least one of CM and a CM remnant in the blood on the basis of a variation of the scattering coefficient.

The method for operating a blood lipid concentration measurement device of the embodiment of the present invention further includes a physical condition determination step of determining a physical condition on the basis of the variation of the concentration of the at least one of CM and a CM remnant.

In the physical condition determination step, a risk of arteriosclerosis is determined from a temporal change in the concentration of the at least one of CM and a CM remnant.

REFERENCE SIGNS LIST 1 blood lipid concentration measurement device
2 irradiation portion
3 light intensity detection portion
4 scattering coefficient calculation portion
5 lipid concentration calculation portion
10 physical condition management measurement device,
101 calculated-value acquisition portion
102 physical condition determination portion
21 irradiation position, 22 light source
31 first light intensity detection portion, 32 second light intensity detection portion
33 detection position, 331 first detection position
332 second detection position
42 light intensity ratio calculation portion, 43 light intensity difference calculation portion

The invention claimed is:
1. A blood particle concentration measurement device comprising:
an irradiation portion configured to irradiate irradiation light having a first wavelength and irradiation light having a second wavelength shorter than the first wavelength at predetermined light intensities toward an inside of a living body from an outside of the living body;

a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion;

a scattering coefficient calculation portion configured to calculate a first scattering coefficient and a second scattering coefficient in the living body respectively on a basis of the first light intensity and the second light intensity detected by the light intensity detection portion; and a particle concentration calculation portion configured to calculate a variation of a concentration of a second particle group in the blood on a basis of a variation of the second scattering coefficient and calculate a variation of a concentration of a first particle group including a particle whose particle diameter is equal to or less than that of a particle included in the second particle group on a basis of a variation of the first scattering coefficient.

2. The blood particle concentration measurement device according to claim 1, wherein the particle concentration calculation portion calculates a variation of a concentration of a particle that is not duplicated between the first particle group and the second particle group from a difference between the variation of the concentration of the first particle group and the variation of the concentration of the second particle group.

3. The blood particle concentration measurement device according to claim 1, further comprising a physical condition determination portion configured to determine a physical condition on a basis of the variation of the concentration of the first particle group and the variation of the concentration of the second particle group.

4. The blood particle concentration measurement device according to claim 3, wherein
the physical condition determination portion determines a course of action to improve a lipid balance from a difference between the variation of the concentration of the first particle group and the variation of the concentration of the second particle group.

5. The blood particle concentration measurement device according to claim 1, wherein
the first wavelength is 750 nm or more and the second wavelength is shorter than the first wavelength and 900 nm or less.

6. The blood particle concentration measurement device according to claim 1, wherein
the first particle group includes at least one of CM and a CM remnant and at least one of VLDL and a VLDL remnant, and the second particle group includes at least one of CM and a CM remnant.

7. The blood particle concentration measurement device according to claim 6, wherein
the physical condition determination portion determines a total absorption amount of alcohol or fats from a temporal change in a concentration of the at least one of VLDL and a VLDL remnant.

8. The blood particle concentration measurement device according to claim 6, wherein
the physical condition determination portion determines a risk of arteriosclerosis from a temporal change in a concentration of the at least one of CM and a CM remnant.

9. The blood particle concentration measurement device according to claim 1, wherein
the irradiation position and a detection position at which the light intensity is detected are arranged apart from each other by a predetermined radiation-detection distance, and the light intensity detection portion detects a light intensity of back scattered light scattered by a particle in the blood.

10. The blood particle concentration measurement device according to claim 1, wherein
the irradiation portion is a light source that emits continuous light, the light source radiates light, and a plurality of the light intensity detection portions disposed at different distances from the irradiation position serving as a substantial center detect light intensities at respective detection positions, and
the scattering coefficient calculation portion calculates a light scattering coefficient in the living body on a basis of a ratio or difference between the respective light intensities detected by the respective light intensity detection portions.

11. A blood lipid concentration measurement device comprising:
an irradiation portion configured to radiate irradiation light having a wavelength of 900 nm or less at a predetermined light intensity toward an inside of a living body from an outside of the living body;
a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion;
a scattering coefficient calculation portion configured to calculate a scattering coefficient in the living body on a basis of the light intensity detected by the light intensity detection portion; and
a lipid concentration calculation portion configured to calculate a variation of only a concentration of at least one of CM and a CM remnant in the blood on a basis of a variation of the scattering coefficient.

12. The blood lipid concentration measurement device according to claim 11, further comprising a physical condition determination portion configured to determine a physical condition on a basis of the variation of the concentration of the at least one of CM and a CM remnant.

13. The blood lipid concentration measurement device according to claim 12, wherein
the physical condition determination portion determines a risk of arteriosclerosis from a temporal change in the concentration of at least one of CM and a CM remnant.

14. A method for operating a blood particle concentration measurement device comprising:
an irradiation step of radiating irradiation light having a first wavelength and irradiation light having a second wavelength shorter than the first wavelength at predetermined light intensities toward an inside of a living body from an outside of the living body;

a light intensity detection step of detecting an intensity of first light and an intensity of second light both emitted from the living body to measure a radiation-detection distance dependent attenuation of light intensities of the radiated irradiation light having the first wavelength and the radiated irradiation light having the second wavelength at a position with a predetermined interval from or continuously to a light irradiation position in the irradiation step;

a scattering coefficient calculation step of calculating a first scattering coefficient and a second scattering coefficient in the living body respectively on a basis of the first light intensity and the second light intensity detected in the light intensity detection step; and a particle concentration calculation step of calculating a variation of a concentration of a second particle group in the blood on a basis of a variation of the second scattering coefficient and calculating a variation of a concentration of a first particle group including a particle whose particle diameter is equal to or less than that of a particle included in the second particle group on a basis of a variation of the first scattering coefficient.

15. The method for operating a blood particle concentration measurement device according to claim 14, wherein
in the particle concentration calculation step, a variation of a concentration of a particle that is not duplicated between the first particle group and the second particle group is calculated from a difference between the variation of the concentration of the first particle group and the variation of the concentration of the second particle group.

16. The method for operating a blood particle concentration measurement device according to claim 14, wherein
the first wavelength is 750 nm or more and the second wavelength is shorter than the first wavelength and 900 nm or less.

17. The method for operating a blood particle concentration measurement device according to claim 14, wherein
the first particle group includes at least one of CM and a CM remnant and at least one of VLDL and a VLDL remnant, and the second particle group includes at least one of CM and a CM remnant.

18. A method for operating a blood lipid concentration measurement device comprising:
an irradiation step of radiating irradiation light having a wavelength of 900 nm or less at a predetermined light intensity toward an inside of a living body from an outside of the living body;
a light intensity detection step of detecting an intensity of light emitted from the living body to measure a radiation-detection distance dependent attenuation of a light intensity of the radiated irradiation light at a position with a predetermined interval from or continuously to a light irradiation position in the irradiation step;
a scattering coefficient calculation step of calculating a scattering coefficient in the living body on a basis of the light intensity detected in the light intensity detection step; and
a lipid concentration calculation step of calculating a variation of a concentration of at least one of CM and a CM remnant in the blood on a basis of a variation of the scattering coefficient.

19. A blood particle concentration measurement device configured to be communicatively connected to a user device, the user device including: an irradiation portion configured to radiate irradiation light having a first wavelength and irradiation light having a second wavelength shorter than the first wavelength at predetermined light intensities toward an inside of a living body from an outside of the living body; a light intensity detection portion configured to detect an intensity of first light and an intensity of second light both emitted from the living body to measure a radiation-detection distance dependent attenuation of light intensities of the radiated irradiation light having the first wavelength and the radiated irradiation light having the second wavelength, the light intensity detection portion being disposed at a predetermined interval from or continuously to a light irradiation position of the irradiation portion; and a communication portion configured to send the first light intensity and the second light intensity detected by the light intensity detection portion, the blood particle concentration measurement device comprising:
a scattering coefficient calculation portion configured to calculate a first scattering coefficient and a second scattering coefficient in the living body respectively on a basis of the first light intensity and the second light intensity sent from the user device; and
a particle concentration calculation portion configured to calculate a variation of a concentration of a second particle group in the blood on a basis of a variation of the second scattering coefficient and calculate a variation of a concentration of a first particle group including a particle whose particle diameter is equal to or less than that of a particle included in the second particle group on a basis of a variation of the first scattering coefficient.

20. A blood lipid concentration measurement device configured to be communicatively connected to a user device, the user device including: an irradiation portion configured to radiate irradiation light having a wavelength of 900 nm or less at a predetermined light intensity toward an inside of a living body from an outside of the living body; a light intensity detection portion configured to detect an intensity of light emitted from the living body to measure a radiation-detection distance dependent attenuation of a light intensity of the radiated irradiation light, the light intensity detection portion being disposed at a predetermined interval from or continuously to a light irradiation position of the irradiation portion; and a communication portion configured to send the light intensity detected by the light intensity detection portion, the blood lipid concentration measurement device comprising:
a scattering coefficient calculation portion configured to calculate a scattering coefficient in the living body on a basis of the light intensity sent from the user device; and
a lipid concentration calculation portion configured to calculate a variation of only a concentration of at least one of CM and a CM remnant in the blood on a basis of a variation of the scattering coefficient.

* * * * *